United States Patent
Cola et al.

(10) Patent No.: US 10,461,015 B2
(45) Date of Patent: Oct. 29, 2019

(54) CARBON NANOTUBE-BASED THERMAL INTERFACE MATERIALS AND METHODS OF MAKING AND USING THEREOF

(71) Applicant: Carbice Corporation, Atlanta, GA (US)

(72) Inventors: Baratunde Cola, Atlanta, GA (US); Craig Green, Atlanta, GA (US); Leonardo Prinzi, Atlanta, GA (US)

(73) Assignee: CARBICE CORPORATION, Atlanta, GA (US)

( * ) Notice: Subject to any disclaimer, the term of this patent is extended or adjusted under 35 U.S.C. 154(b) by 0 days.

(21) Appl. No.: 15/913,534

(22) Filed: Mar. 6, 2018

(65) Prior Publication Data

US 2018/0254236 A1 Sep. 6, 2018

Related U.S. Application Data

(60) Provisional application No. 62/467,649, filed on Mar. 6, 2017.

(51) Int. Cl.
| | |
|---|---|
| *H01L 23/373* | (2006.01) |
| *H05K 7/20* | (2006.01) |
| *H01L 23/00* | (2006.01) |
| *B82Y 30/00* | (2011.01) |
| *G01R 31/28* | (2006.01) |

(Continued)

(52) U.S. Cl.
CPC .......... *H01L 23/3735* (2013.01); *B82Y 30/00* (2013.01); *C09K 5/14* (2013.01); *G01N 25/18* (2013.01); *G01R 31/2896* (2013.01); *H01L 23/3731* (2013.01); *H01L 24/48* (2013.01); *H05K 7/20481* (2013.01); *B82Y 40/00* (2013.01); *C01B 2202/24* (2013.01);
(Continued)

(58) Field of Classification Search
None
See application file for complete search history.

(56) References Cited

U.S. PATENT DOCUMENTS

| | | | |
|---|---|---|---|
| 2,243,979 A | | 6/1941 | Reynolds |
| 6,142,662 A | * | 11/2000 | Narh ...................... G01N 25/18 374/29 |

(Continued)

FOREIGN PATENT DOCUMENTS

| | | |
|---|---|---|
| EP | 2251302 | 11/2010 |
| JP | 2013115094 | 6/2013 |
| WO | 2013007645 | 1/2013 |

OTHER PUBLICATIONS

Green et al., Design and evaluation of polymer-carbon nanotube composites for reliable, low resistance, static and dynamic thermal interface materials, 2016 15th IEEE Intersociety Conference on Thermal and Thermomechanical Phenomena in Electronic Systems (ITherm). (Year: 2016).*

(Continued)

*Primary Examiner* — Andres Munoz
(74) *Attorney, Agent, or Firm* — Pabst Patent Group LLP

(57) ABSTRACT

Single-layer CNT composites and multilayered or multi-tiered structures formed therefrom, by stacking of vertically aligned carbon nanotube (CNT) arrays, and methods of making and using thereof are described herein. Such multilayered or multitiered structures can be used as thermal interface materials (TIMs) for a variety of applications, such as burn-in testing.

39 Claims, 10 Drawing Sheets

(51) Int. Cl.
*C09K 5/14* (2006.01)
*G01N 25/18* (2006.01)
*B82Y 40/00* (2011.01)

(52) U.S. Cl.
CPC ............. *H05K 2201/026* (2013.01); *H05K 2201/10151* (2013.01)

(56) References Cited

U.S. PATENT DOCUMENTS

| | | | |
|---|---|---|---|
| 6,250,127 B1 | 6/2001 | Polese | |
| 6,921,462 B2 | 7/2005 | Montgomery | |
| 6,965,513 B2 | 11/2005 | Montgomery | |
| 7,086,451 B2 | 8/2006 | Leu | |
| 7,465,605 B2 | 12/2008 | Raravikar | |
| 8,093,715 B2 | 1/2012 | Xu | |
| 8,220,530 B2 | 7/2012 | Cola | |
| 2002/0140336 A1 | 10/2002 | Stoner | |
| 2004/0065717 A1 | 4/2004 | Saijo | |
| 2004/0105807 A1 | 6/2004 | Fan | |
| 2004/0184981 A1 | 9/2004 | Liu | |
| 2004/0261987 A1 | 12/2004 | Zhang | |
| 2005/0058178 A1* | 3/2005 | Shih | G01N 3/18 374/51 |
| 2005/0150887 A1* | 7/2005 | Taya | B82Y 10/00 219/548 |
| 2005/0214197 A1 | 9/2005 | Gu | |
| 2005/0228097 A1 | 10/2005 | Zhong | |
| 2006/0073089 A1 | 4/2006 | Ajayan | |
| 2006/0231970 A1 | 10/2006 | Huang | |
| 2007/0253889 A1 | 11/2007 | Awano | |
| 2008/0075137 A1* | 3/2008 | Cervantes | G01N 25/18 374/1 |
| 2008/0095695 A1 | 4/2008 | Shanov | |
| 2008/0149166 A1 | 6/2008 | Beeson | |
| 2008/0160866 A1 | 7/2008 | Zhang | |
| 2008/0236804 A1 | 10/2008 | Cola | |
| 2008/0241755 A1 | 10/2008 | Franklin | |
| 2008/0292840 A1 | 11/2008 | Majumdar | |
| 2009/0032496 A1 | 2/2009 | Yao | |
| 2009/0246507 A1 | 10/2009 | Graham | |
| 2010/0027221 A1 | 2/2010 | Iwai | |
| 2011/0020593 A1 | 1/2011 | Winkler | |
| 2011/0086464 A1 | 4/2011 | Kim | |
| 2012/0128880 A1 | 5/2012 | Talapatra | |
| 2013/0234313 A1 | 9/2013 | Wainerdi | |
| 2014/0015158 A1 | 1/2014 | Cola | |
| 2014/0286373 A1* | 9/2014 | Thresher | G01N 25/18 374/29 |

OTHER PUBLICATIONS

Bayer, et al., Support-Catalyst-Gas interactions during carbon nanotube growth on metallic ta films, J Phys. Chem., 115:4359-69 (2011).

Cola, et al., "Contact mechanics and thermal conductance of carbon nanotube array interfaces", Int. J. Heat Mass Trans., 52:3490-3503 (2009).

Hildreth, et al., "Conformally coating vertically aligned carbon nanotube arrays using thermal decomposition of iron pentacarbonyl", J Vac Sci Technol. B, 30(3):03D1011-03D1013 (2012).

Dai, et al., "Controlled growth and modification of vertically-aligned carbon nanotubes for multifunctional applications", Mater. Sci. Eng., 70:63-91 (2010).

Kim, et al., "Evolution in catalyst morphology leads to carbon nanotube growth termination", J Phys. Chem. Lett, 1:918-22 (2010).

* cited by examiner

CARBON NANOTUBE-BASED THERMAL INTERFACE MATERIALS AND METHODS OF MAKING AND USING THEREOF

CROSS-REFERENCE TO RELATED APPLICATIONS

This application claims benefit of and priority to U.S. Provisional Application No. 62/467,649, filed on Mar. 6, 2017, which is hereby incorporated herein by reference in its entirety.

FIELD OF THE INVENTION

This invention is in the field of carbon nanotube arrays or sheets, particularly arrays or sheets which can be single-layered or stacked to form multilayered or multitiered structures and methods of making and using thereof.

BACKGROUND OF THE INVENTION

As the performance and packaging demands on modern electronics have continued to become more and more aggressive, identifying new thermal solutions has become a critical part of the design process. In nearly all thermal management applications, there are numerous heat transfer interfaces where intimate contact is needed to ensure efficient removal of heat from the package. In this space, a wide variety of thermal interface materials (TIMs) have been developed for specific applications (R. Prasher, "Thermal interface materials: historical perspective, status, and future directions," *Proceedings of the IEEE*, vol. 94, pp. 1571-1586, 2006).

Carbon nanotube (CNT) arrays are an attractive solution for enhancing thermal transport between surfaces. CNTs can be grown on metal substrates, eliminating concerns associated with pump out or voiding that liquid thermal interface materials (TIMs) and greases may suffer from.

The high in-plane conductivity of individual nanotubes (as high as 3,000 W/m-K) means that even at relatively low CNT densities (typical CNT fill factors are on the order of 1%) the cross plane thermal conductance of a CNT-based TIM can be competitive with that of thermal grease. Furthermore, the favorable deformation mechanics of CNTs allow them to efficiently conform to the asperities of adjoining surfaces, resulting in high contact areas at such interfaces between surfaces.

A key challenge, however, in CNT-based TIMs comes from the difficulty in growing very long CNTs on metal substrates. Unlike CNTs grown on silicon or other inert substrates, the catalyst required for CNT growth suffers from subsurface diffusion when grown on metal substrates, resulting in early termination of tube growth. Furthermore, defects tend to accumulate in CNTs as their height increases, resulting in CNT arrays with conductivities significantly lower than the 3,000 W/m-K limit otherwise achievable with pristine tubes.

Thus, there is a need for overcoming the above-mentioned difficulty in growing long CNT arrays on metal substrates and methods of making materials which have good thermal transport properties.

Therefore, it is an object of the invention to provide CNT arrays or sheets and structures formed thereof and methods of making such structures having good thermal transport properties.

It is also an object of the invention to provide CNT arrays or sheets and structures formed thereof which can provide high levels of compliance at the interface with one or more surfaces.

It is a further object of the invention to provide TIM composites with improved durability needed for burn-in applications.

It is also an object of the invention to provide TIM composites with good compliance and compression properties that allow the size of a device under testing to be changed.

SUMMARY OF THE INVENTION

Single layered or multilayered or multitiered structures, formed by stacking of vertically aligned carbon nanotube (CNT) arrays, and methods of making and using thereof are described herein.

In some embodiments described, two or more CNT arrays are stacked to form multilayered or multitiered structures. Multiple CNT arrays can be stacked, such that the nanostructure elements from opposing arrays form into tiers in the stack and become at least partially interdigitated with one another. Unlike the stacking of a traditional material, stacked arrays of vertically aligned nanostructures do not suffer from a linear (or worse) increase in thermal resistance with increasing thickness. Accordingly, the resulting multilayered structures can mitigate the adverse impact of thickness and boundaries on energy transport as a result of the interdigitation of the nanostructure elements (i.e., CNTs) of the two or more arrays when contacted. In contrast, for a typical material the resistance to heat transfer is directly proportional to the material's thickness, with an additional interfacial resistance at the interfaces of a multilayered structure.

For multilayered or multitiered structures formed by stacking of vertically aligned nanostructure materials of CNT arrays, wherein the CNTs of the arrays at least partially interdigitate within or into one another, effectively increasing the density of the CNTs. Typically, the density of CNTs grown on metal substrates is only about 1% of the total volume. When two adjacent layers of CNT arrays are stacked, for example, the density of heat conducting elements, such as CNTs or structures formed thereof, is effectively doubled. As such the resistance to heat transfer per unit length is reduced in kind.

An advantage of the multilayered or multitiered structures formed by stacking of two or more CNT arrays over traditional bulk materials comes at the interface of the arrays. For example, resistance to heat transfer increases not only due to the increase in thickness of a multilayer stack, but also due to the interfacial resistances between the tiers. Accordingly, between any two adjacent tiers, the boundary between the two tiers is the location of poor heat transfer, relative to the bulk material due to poor contact between the tiers, as well as due to scattering of energy carriers (e.g. electrons or phonons) at the boundary. When interdigitated, the high aspect ratio of the nanostructures, such as CNTs, results in a very high contact area between the tiers minimizing the poor contact area contribution to the inter tier interfacial resistance. Although Kapitza (scattering) resistance cannot be completely eliminated the resistance can be reduced by applying, infiltrating, or backfilling the array or sheet with a polymer, wax, or other secondary material that facilitates thermal/energy transport across the boundary. This transport facilitation may be through the formation of a covalent or weak atomic interaction between the CNT and a secondary material, reduction of acoustic phononic transport mismatch relative to air, or other types of mechanisms.

In some embodiments, nanostructure elements which form the array are vertically aligned carbon nanotubes (CNTs). In some embodiments, the CNT array is grown on a metal substrate which is formed of aluminum, copper or steel or comprises aluminum, copper or steel, or alloys thereof. In another embodiment, the CNT array is formed on a flexible, electrically and thermally conductive substrate, such as graphite. In yet another embodiment, the CNT array is grown on an electrically insulating substrate, such as a flexible ceramic. In one embodiment, the inert support for the CNT array is a piece of metal foil, such as aluminum foil. In some instances only one surface (i.e., side) of the metal foil contains an array of vertically aligned CNTs anchored to the surface or the substrate/support. In other cases, both surfaces (i.e., sides) of the substrate/support, such as a metal foil, contain a coated array of aligned CNTs anchored to the surface. As another example, CNT sheets can be coated on one or both sides and do not require an inert support.

In certain embodiments, a single substrate containing thereon one or more CNT arrays on one or more surfaces, as described herein. In other embodiments, two or more CNT arrays are stacked atop one another and the nanostructure elements of the individual arrays, such as the CNTs or some portion thereof, fully or substantially interdigitate within one another; "substantially," as used herein, refers to at least 95%, 96%, 97%, 98%, or 99% interdigitation between the nanostructure elements (i.e., CNTs) of the individual arrays. In some embodiments, the extent of interdigitation is in the range of about 0.1% to 99% or at least about 1%, 5%, 10%, 20%, 30%, 40%, 50%, 60%, 70%, 80%, 90%, or 95%. In certain other embodiments, the two CNT arrays may be interdigitated only at the tips of the nanostructure elements (i.e., CNTs) of the individual arrays. By stacking two or more individual CNT arrays, wherein the nanostructure elements of the individual arrays interdigitate when stacked adjacently, it is possible to form multilayered or multitiered structures.

In certain embodiments, one or more individual nanostructure elements, such as CNTs, of the array may navigate through another when adjacent CNT arrays are brought in contact during the stacking process.

In some embodiments, the individual nanostructure elements, such as CNTs, of the array may interdigitate and form into larger structures, such as superstructures, such as, but not limited to, tube bundles, clumps, or rows. Such superstructures may be formed through mechanisms such as capillary clumping or when a polymer coating has been applied to the CNT arrays prior to, during, or following the stacking process.

In certain embodiments, adjacent tiers formed by stacking of CNT arrays are formed via simple dry contact, using entanglement, friction or weak attraction forces between the nanostructures present therein to keep the resulting interdigitated structure together.

In certain other embodiments the CNT arrays on a substrate, alone or as part of a multilayered stack resulting therefrom may optionally be infiltrated or backfilled with a polymer, wax, liquid metal, or other suitable material that solidifies inside the stacked structure in order to hold the interdigitated arrays together.

In some embodiments the polymer, wax, liquid metal, or other suitable material can reduce the transport resistance between the multiple layers or tiers formed, resulting from improved contact area, a reduction in scattering, or other related mechanisms. In yet other embodiment the tiers formed by stacking of arrays may be bonded by use of an adhesive or a phase-change material.

CNT arrays and the multilayered or multitiered structures formed by stacking of such CNT arrays exhibit both high thermal conductance and mechanical durability. The multilayered or multitiered structures formed by stacking of CNT arrays described herein can be used as thermal interface materials (TIMs). Accordingly, such materials are well suited for applications where repeated cycling is required. For example, they can be employed as thermal interface materials during 'burn-in' testing of electrical components, such as chips. In some embodiments, the inert support/substrate is a surface of a conventional metal heat sink or spreader. This functionalized heat sink or spreader may then be abutted or adhered to a heat source, such as an integrated circuit package. Such TIM materials can also be placed or affixed in between a heat source and a heat sink or heat spreader, such as between an integrated circuit package and a finned heat exchanger, to improve the transfer of heat from the heat source to the heat sink or spreader.

The CNT arrays and the multilayered or multitiered structures formed by stacking of such CNT arrays described herein can be used as thermal interface materials (TIMs) in personal computers, server computers, memory modules, graphics chips, radar and radio-frequency (RF) devices, disc drives, displays, including light-emitting diode (LED) displays, lighting systems, automotive control units, power-electronics, solar cells, batteries, communications equipment, such as cellular phones, thermoelectric generators, and imaging equipment, including MRIs.

In certain embodiments, the single-layered CNT arrays or multilayered or multitiered structures formed by stacking of CNT arrays are useful as TIMs in low contact pressure and/or low ambient pressure applications, such as in aerospace applications where such TIMs could be used in satellites or space vehicles/systems. In certain embodiments, the multilayered or multitiered structures formed by stacking of CNT arrays are useful at temperatures below ambient, below freezing, or at cryogenic temperatures (such as experienced in space).

The CNT arrays and the multilayered or multitiered structures formed by stacking of such CNT arrays described herein can also be used for applications other than heat transfer. Examples include, but are not limited to, microelectronics, through-wafer vertical interconnect assemblies, and electrodes for batteries and capacitors. Currently, copper and aluminum foil are used as the backing materials for the anode and cathode in lithium ion batteries. The CNT arrays and multilayered or multitiered structures formed by stacking of such CNT arrays could also be used for electromagnetic shielding.

The CNT arrays and multilayered or multitiered structures formed therefrom are useful as TIMs used in thermal management methods, such as in a method including the steps of:

(1) attaching the substrate directly to a thermal or electrical unit head to cover the area of the head completely or matching the size of the device under test;

(2) engaging the thermal or electrical unit head with the attached substrate to the device under test with a pressure of at least 10 psi and engagement temperature less than 150° C.;

(3) holding the engagement under the pressure of at least 10 psi for at least 5 minutes or cycling the engagement at least one to five times, wherein during each engagement the device under test is powering up and heating the thermal or electrical unit head to simulate the device powering up to reach a temperature of at least 50° C.;

(4) disengaging and re-engaging the thermal or electrical head and substrate with the device under test for at least 1,500 cycles of powering up; and (5) testing the device under test; in order to determine the thermal resistance and/or relative thermal resistance following cycling.

The CNT arrays and multilayered or multitiered structures formed therefrom used as TIMs for burn in or other applications may also be provided in suitable kits.

BRIEF DESCRIPTION OF THE DRAWINGS

FIG. 5A shows a manually applied paraffin wax coat and FIG. 5B shows a powder coated synthetic wax.

FIG. 6A shows the system where the upper bar engaged with the lower bar and the lower bar is heated using cartridge heaters and the upper bar is actively cooled with chilled water, with thermocouples placed along the bars to monitor the temperature. FIGS. 6B and 6C show detailed side views of the lower and upper burn-in system bars.

DETAILED DESCRIPTION OF THE INVENTION

I. Definitions

Figure 1:
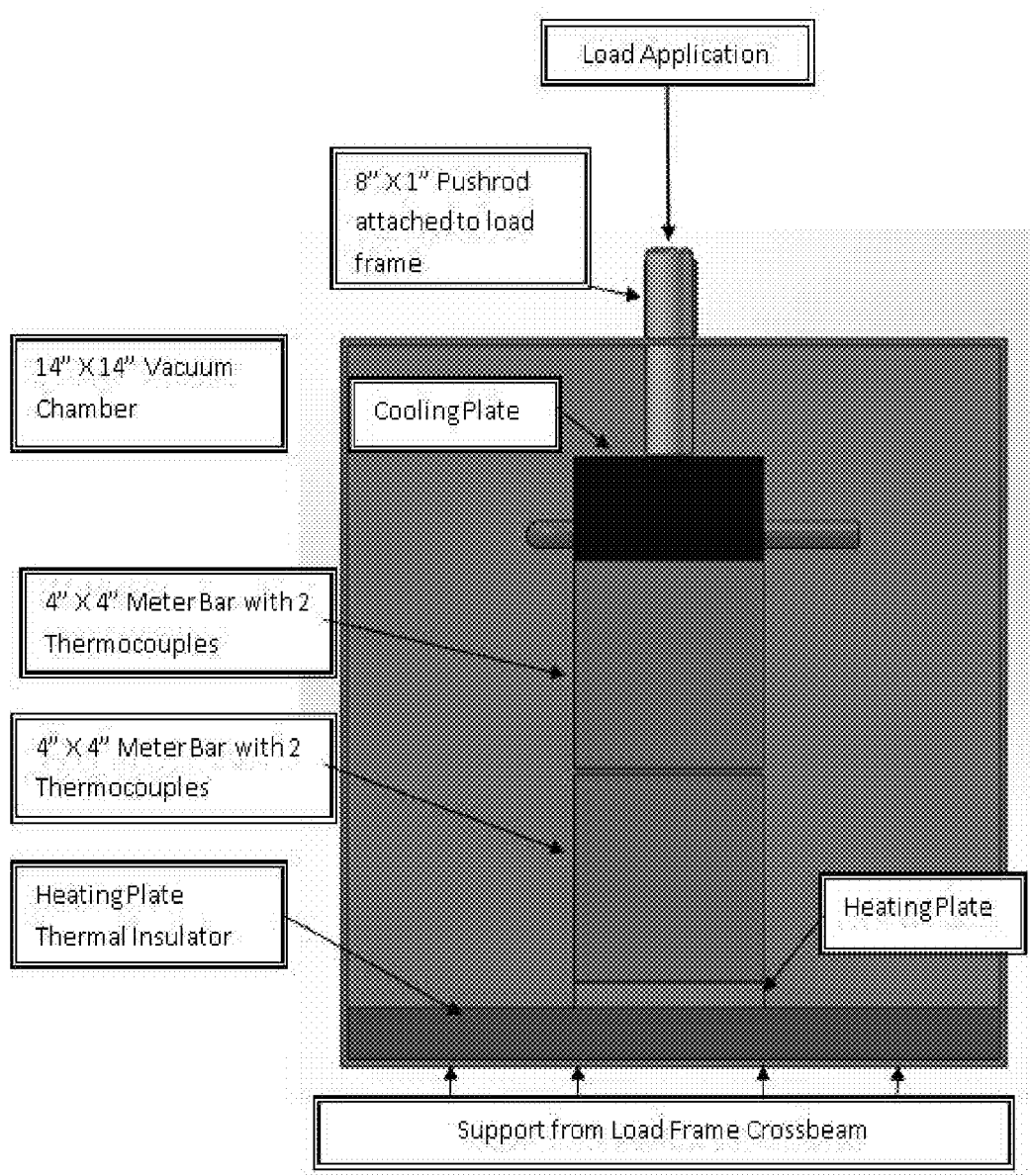
FIG. 1 is a non-limiting schematic diagram of thermal interface material test fixture in vacuum chamber.

"Thermal Interface Material" (TIM), as used herein, refers to a material or combination of materials that provide high thermal conductance and mechanical compliance between a heat source and heat sink or spreader to effectively conduct heat away from a heat source.

"Compliant" or "Compliance," as used herein, refers to the ability of a material to conform when contacted to one or more surfaces such that efficient conformance to the asperities of the adjoining surface results in sufficient or high contact areas at the interfaces between the surfaces and the material.

"Interdigitation" or "Interdigitating", as used herein, refers to the ability and or degree which one or more individual nanostructure elements of an array or sheet to infiltrate or penetrate into the adjacent nanostructure elements of another array or sheet when the two different arrays or sheets are contacted or stacked.

"Carbon Nanotube Array" or "CNT array" or "CNT forest", as used herein, refers to a plurality of carbon nanotubes which are vertically aligned on a surface of a material. Carbon nanotubes are said to be "vertically aligned" when they are substantially perpendicular to the surface on which they are supported or attached. Nanotubes are said to be substantially perpendicular when they are oriented on average within 30, 25, 20, 15, 10, or 5 degrees of the surface normal.

"Carbon Nanotube Sheet" or "CNT sheet", as used herein, refers to a plurality of carbon nanotubes which are aligned in plane to create a freestanding sheet. Carbon nanotubes are said to be "aligned in plane" when they are substantially parallel to the surface of the sheet that they form. Nanotubes are said to be substantially parallel when they are oriented on average greater than 40, 50, 60, 70, 80, or 85 degrees from sheet surface normal.

"Coating material" as used herein, generally refers to polymers and/or molecules that can bond to CNTs through van der Waals bonds, π-π stacking, mechanical wrapping and/or covalent bonds and bond to metal, metal oxide, or semiconductor material surfaces through van der Waals bonds, π-π stacking, and/or covalent bonds.

Numerical ranges disclosed in the present application include, but are not limited to, ranges of temperatures, ranges of pressures, ranges of molecular weights, ranges of integers, ranges of conductance and resistance values, ranges of times, and ranges of thicknesses. The disclosed ranges of any type, disclose individually each possible number that such a range could reasonably encompass, as well as any sub-ranges and combinations of sub-ranges encompassed therein. For example, disclosure of a pressure range is intended to disclose individually every possible temperature value that such a range could encompass, consistent with the disclosure herein.

II. Coated Carbon Nanotube Arrays or Sheets

A. Carbon Nanotube Arrays

Carbon nanotube arrays are described herein contain a plurality of carbon nanotubes supported on, or attached to, the surface of an inert substrate/support, such as a metallic (e.g., Al or Au) foil, metal alloys (i.e., steel). In some embodiments, the substrate/support can be a flexible, electrically, and thermally conductive substrate, such as graphite or other carbon-based material. In yet other embodiments, the substrate/support can be an electrically insulating substrate such as a flexible ceramic. The CNT arrays can be formed using the methods described below. The CNTs are vertically aligned on the substrate/support. CNTs are said to be "vertically aligned" when they are substantially perpendicular to the surface on which they are supported or attached. Nanotubes are said to be substantially perpendicular when they are oriented on average within 30, 25, 20, 15, 10, or 5 degrees of the surface normal.

Generally, the nanotubes are present at a sufficient density such that the nanotubes are self-supporting and adopt a substantially perpendicular orientation to the surface of the multilayer substrate. Preferably, the nanotubes are spaced at optimal distances from one another and are of uniform height to minimize thermal transfer losses, thereby maximizing their collective thermal diffusivity.

The CNT arrays contain nanotubes which are continuous from the top of the array (i.e., the surface formed by the distal end of the carbon nanotubes when vertically aligned on the multilayer substrate) to bottom of the array (i.e., the surface of the multilayer substrate). The array may be formed from multi-wall carbon nanotubes (MWNTs), which generally refers to nanotubes having between approximately 4 and approximately 10 walls. The array may also be formed from few-wall nanotubes (FWNTs), which generally refer to nanotubes containing approximately 1-3 walls. FWNTs include single-wall carbon nanotubes (SWNTs), double-wall carbon nanotubes (DWNTS), and triple-wall carbon nanotubes (TWNTs). In certain embodiments, the nanotubes are MWNTs. In some embodiments, the diameter of MWNTs in the arrays ranges from 10 to 40 nm, more preferably 15 to 30 nm, most preferably about 20 nm. The length of CNTs in the arrays can range from 1 to 5,000 micrometers, preferably 5 to 5000 micrometers, preferably 5 to 2500 micrometers, more preferably 5 to 2000 micrometers, more preferably 5 to 1000 micrometers. In some embodiments, the length of CNTs in the arrays can range from 1-500 micrometers, even more preferably 1-100 micrometers.

The CNTs display strong adhesion to the multilayer substrate. In certain embodiments, the CNT array or sheet will remain substantially intact after being immersed in a solvent, such as ethanol, and sonicated for a period of at least five minutes. In particular embodiments, at least about 90%, 95%, 96%, 97%, 98%, 99%, or 99.9% of the CNTs remain on the surface after sonication in ethanol.

B. Carbon Nanotube Sheets

Carbon nanotube sheets are also described herein. The sheets contain a plurality of carbon nanotubes that support each other through strong van der Waals force interactions and mechanical entanglement to form a freestanding material. The CNT sheets can be formed using the methods described below. The CNTs form a freestanding sheet and are aligned in plane with the surface of this sheet. CNTs are said to be "aligned in plane" when they are substantially parallel to the surface of the sheet that they form. Nanotubes are said to be substantially parallel when they are oriented on average greater than 40, 50, 60, 70, 80, or 85 degrees from sheet surface normal.

Generally, the nanotubes are present at a sufficient density such that the nanotubes are self-supporting and adopt a substantially parallel orientation to the surface of the sheet. Preferably, the nanotubes are spaced at optimal distances from one another and are of uniform length to minimize thermal transfer losses, thereby maximizing their collective thermal diffusivity.

The CNT sheets may be formed from multi-wall carbon nanotubes (MWNTs), which generally refers to nanotubes having between approximately 4 and approximately 10 walls. The sheets may also be formed from few-wall nanotubes (FWNTs), which generally refer to nanotubes containing approximately 1-3 walls. FWNTs include single-wall carbon nanotubes (SWNTs), double-wall carbon nanotubes (DWNTS), and triple-wall carbon nanotubes (TWNTs). In certain embodiments, the nanotubes are MWNTs. In some embodiments, the diameter of MWNTs in the arrays ranges from 10 to 40 nm, more preferably 15 to 30 nm, most preferably about 20 nm. The length of CNTs in the sheets can range from 1 to 5,000 micrometers, preferably 100 to 5000 micrometers, preferably 500 to 5000 micrometers, more preferably 1000 to 5000 micrometers. In some embodiments, the length of CNTs in the sheets can range from 1-500 micrometers, even more preferably 1-100 micrometers.

C. Coating(s)/Coating Materials

The CNT array or sheet can include a coating or coating material (terms can be used interchangeably) which adheres or is bonded to the CNTs. The coating/coating material can be applied as described below. In some embodiments, the coating contains one or more oligomeric materials, polymeric materials, waxes (such as polyethylene waxes), or combinations thereof. The polymeric material's hardness, thermal stability, and shear strength can be selected to provide improved durability and performance during burn-in applications. In some embodiments, the coating or coating material is a polymer-based encapsulant which maximizes durability and improves the interface contact area.

In other embodiments, the coating contains one or more non-polymeric materials. In some embodiments, the coating can contain a mixture of oligomeric, waxes (such as polyethylene waxes), and/or polymeric material and non-polymeric materials. The polymeric material's hardness, thermal stability, and shear strength can be selected to provide improved durability and performance during burn-in applications.

In certain embodiments, the coating material(s) act as a bonding agent(s) which can bonded, such as chemically, the carbon nanotubes of the stacked arrays or sheets. Without limitation, such coating material(s) which can act as bonding agents(s) can be selected from adhesives (i.e., acrylate adhesives) and a phase change material (i.e., a wax or waxes).

In some embodiments, the coating which adheres or is bonded to the CNTs of an array is applied before two or more CNT arrays or sheets are stacked while in other embodiments, the coating which adheres or is bonded to the CNTs of an array is applied following stacking of two or more CNT arrays or sheets. In yet other embodiments, the coating is infiltrated or backfilled into multilayered or multitiered structures formed of stacked CNT arrays or sheets and adheres or is bonded to the CNTs of the arrays forming the structure. As used herein, "infiltration" or "infiltrated" refer to a coating material(s) which are permeated through at least some of the carbon nanotubes of the arrays or sheets which were stacked to form the multilayered or multitiered structures. In some embodiments, the extent of infiltration is in the range of 0.1-99.9%. In some embodiments, the infiltrated coating material at least partially fills the interstitial space between carbon nanotubes while in some other embodiments the infiltrated coating coats at least some of the surfaces of the carbon nanotubes, or both. In some embodiments, the infiltrated coating material fills the all or substantially all (i.e., at least about 95%, 96%, 97%, 98%, or 99%) of the interstitial space between carbon nanotubes present in the tiers or layers of the structure formed by stacking of the CNT arrays or sheets.

A variety of materials can be coated onto the CNT arrays or sheets, prior to stacking, during stacking, or following stacking. In particular embodiments, the coatings can cause a decrease in the thermal resistance of the CNTs of arrays or sheets of structure having a plurality of layers or tiers, as defined herein.

The coating or coating materials described can be applied conformally and uniformly to coat the tips and/or sidewalls of the CNTs of the arrays formed on a substrate and/or multilayered stacks thereof. "Conformally," as used herein refers to a uniform coating, which is pin-hole free or substantially pin-hole free (i.e., having less than 10%, 9%, 8%, 7%, 6%, 5%, 4%, 3%, 2%, 1% pin-holes), on the tips and/or side-walls of the vertically aligned CNTs attached to a substrate or multilayered stacks thereof. Conformal coatings may be less than about 30 nm, 25 nm, 20 nm, 15 nm, 10 nm, 9 nm, 8 nm, 7 nm, 6 nm, 5 nm, 4 nm, 3 nm, 2 nm, or 1 nm. The conformal coating may have a thickness of between about 1 nm to 30 nm. In certain embodiments, the conformal coating is an adhesive (see more detailed discussion below) that allows for adherence of the CNT arrays to a substrate, such as a heat sink, for thermal management and for burn-in applications.

It is also desirable that the coating be reflowable as the interface is assembled using, for example, solvent, heat or some other easy to apply source. Polymers used as coatings must be thermally stable up to at least 130° C. In some embodiments, the coating is readily removable, such as by heat or dissolution in a solvent, to allow for "reworking" of the interface. "Reworking", as used herein, refers to breaking the interface (i.e., removing the coating) by applying solvent or heat.

1. Polymeric Coating Materials

In some embodiments, the coating is, or contains, one or more polymeric materials. The polymer coating can contain a conjugated polymer, such as an aromatic, heteroaromatic, or non-aromatic polymer, or a non-conjugated polymer.

Suitable classes of conjugated polymers include polyaromatic and polyheteroaromatics including, but not limited to, polythiophenes (including alkyl-substituted polythiophenes), polystyrenes, polypyrroles, polyacetylenes, polyanilines, polyfluorenes, polyphenylenes, polypyrenes, polyazulenes, polynaphthalenes, polycarbazoles, polyindoles, polyazepines, poly(3,4-ethylenedioxythiophenes), poly(p-phenyl sulfides), and poly(p-phenylene vinylene). Suitable non-aromatic, conjugated polymers include, but are not limited to, polyacetylenes and polydiacetylenes. The polymer classes listed above include substituted polymers, wherein the polymer backbone is substituted with one or more functional groups, such as alkyl groups. In some embodiments, the polymer is polystyrene (PS). In other embodiments, the polymer is poly(3-hexythiophene) (P3HT). In other embodiments, the polymer is poly(3,4-3thylenedioxythiophene) (PEDOT) or poly(3,4-3thylenedioxythiophene) poly(styrenesulfonate) (PEDOT:PSS).

In other embodiments, the polymer is a non-conjugated polymer. Suitable non-conjugated include, but are not limited to, polyvinyl alcohols (PVA), poly(methyl methacrylates) (PMMA), polydimethylsiloxanes (PDMS), polyurethane, silicones, acrylics, and combinations (blends) thereof.

In other embodiments, the polymer is a paraffin wax. In other embodiments, the polymer is a synthetic wax such as Fischer-Tropsch waxes or polyethylene waxes. In other embodiments, the polymer is a wax that has a melting temperature above 80, 90, 100, 110, or 120° C., preferably above 130° C.

Polymeric materials, including waxes (such as polyethylene waxes) may have any suitable weight average molecular weight, such as but not limited to, 1,000 Daltons to 1,000,000 Daltons, 1,000 Daltons to 500,000 Daltons, 1,000 Daltons to 250,000 Daltons, 1,000 Daltons to 100,000 Daltons, 1,000 Daltons to 75,000 Daltons, 1,000 Daltons to 50,000 Daltons, 1,000 Daltons to 25,000 Daltons, or 1,000 Daltons to 10,000 Daltons. In some embodiments, combinations of different polymeric materials having any combination of weight average molecular weights may be used to infiltrate and/or applied conformally to coat the tips and/or sidewalls of the CNTs of the arrays on a substrate or stacks formed therefrom. In preferred embodiments, a combination of high and low weight average molecular weight polymers may be used to afford optimal hardness, thermal stability, and shear strength to provide improved durability and performance during burn-in of TIMs formed from the CNT arrays described herein.

In yet other embodiments, the polymer is a hot glue or hot melt adhesive that combines wax, tackifiers and a polymer base to provide improved surface adhesion. In other embodiments, the polymer is a pressure sensitive adhesive.

D. Other Coating Materials

1. Metallic Nanoparticles

The CNT arrays or sheets can additionally be coated with one or more metal nanoparticles. One or more metal nanoparticles may be adsorbed to the distal ends and/or sidewalls of the CNTs to bond the distal ends and/or sidewalls of the CNTs to a surface, reduce thermal resistance between the CNT array or sheet and a surface, or combinations thereof. Metal nanoparticles can be applied to CNT arrays or sheets using a variety of methods known in the art.

Examples of suitable metal nanoparticles include palladium, gold, silver, titanium, iron, nickel, copper, and combinations thereof.

2. Flowable or Phase Change Materials

In certain embodiments, flowable or phase change materials are applied to the CNT arrays or sheets prior to stacking, during stacking, or following stacking. Flowable or phase change materials may be added to the CNT array or sheet to displace the air between CNTs and improve contact between the distal ends and/or sidewalls of CNTs and a surface, and as a result reduce thermal resistance of the array or sheet and the contact between the array or sheet and a surface, or combinations thereof. Flowable or phase change materials can be applied to CNT arrays using a variety of methods known in the art.

Examples of suitable flowable or phase change materials include paraffin waxes, polyethylene waxes, hydrocarbon-based waxes in general, and blends thereof. Other examples of suitable flowable or phase change materials that are neither wax nor polymeric include liquid metals, oils, organic-inorganic and inorganic-inorganic eutectics, and blends thereof. In some embodiments, the coating material, such as a non-polymeric coating material and the flowable or phase change material are the same material or materials.

III. Multilayered or Multitiered Structures

Figure 2:
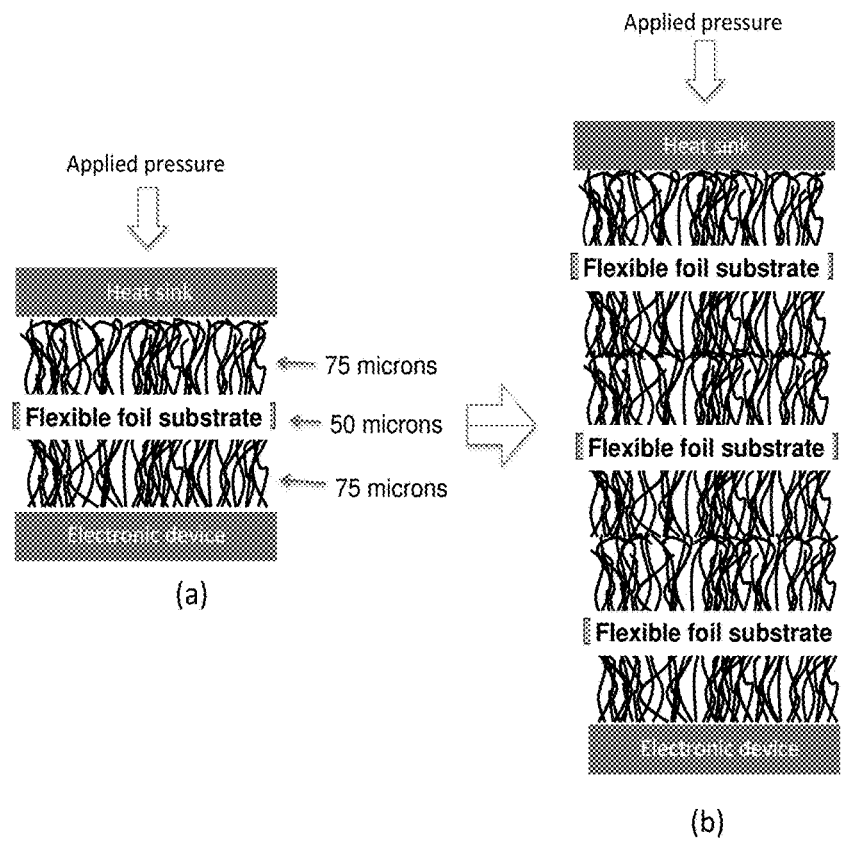
FIG. 2 is a non-limiting schematic of a multilayered/multitiered structure formed by stacking of carbon nanotube (CNT) arrays.

The single-layer CNT arrays or sheets having arrays on one or both surfaces of a substrate, as described above, can be stacked according to the methods described below to afford multilayered or multitiered structures. A non-limiting example of a three layered/tiered structure is shown in the schematic of FIG. 2 (right side). A layer or tier is formed by contacting/stacking the carbon nanotubes of two CNT arrays or sheets, which interdigitate at least partially, and which may optionally be coated with a suitable coating material as described herein.

In some embodiments the multilayered or multitiered structures can further include a coating, a coating of metallic nanoparticles, and/or a coating of flowable or phase change materials on the nanostructure elements, such as CNTs, of the arrays.

At least two CNT arrays or sheets can be stacked to form the multilayered or multitiered structures. For example, FIG. 2 shows stacking of three CNT arrays (right side). By using more CNT arrays the thickness of the multilayered or multitiered structures can be increased as needed. In some embodiments, up to 5, 10, 15, 20, 25, 30, or more CNT arrays or sheets can be stacked according to the method described above. The thickness of the resulting multilayered or multitiered structures formed by stacking can be in the range 1-10,000 microns or more. In some embodiments, the thickness of the resulting multilayered or multitiered structures formed by stacking can be 1-3,000 micrometers, even more preferably 70-3,000 micrometers. In some embodiments, the number of layers and/or thickness is based on the thickness of the CNT forest formed on the arrays used in the stacking process.

In a non-limiting embodiment, at least two vertically aligned arrays or sheets formed on supports/substrates are stacked/contacted such that the nanostructure elements, such as CNTs, of the arrays at least partially interdigitate on contact. In one embodiment full interdigitation of nanostructure elements of the arrays occurs within one another when stacked. In other embodiments the arrays may interdigitate only at the tips of the nanostructure elements, such as CNTs. In yet other embodiments, the individual nanostructures can navigate through the nanostructures of the adjacent array during the interdigitating process and the nanostructure elements of the individual arrays, such as the CNTs or some portion thereof, fully or substantially interdigitate within one another; "substantially," as used herein, refers to at least 95%, 96%, 97%, 98%, or 99% interdigitation between the nanostructure elements of the individual arrays. In some embodiments, the extent of interdigitation is in the range of about 0.1% to 99% or at least about 1%, 5%, 10%, 20%, 30%, 40%, 50%, 60%, 70%, 80%, 90%, or 95%.

In some embodiments the nanostructures of the stacked arrays, which interdigitate at least partially, may also form into larger superstructures, such as, but not limited to, tube bundles, clumps, or rows. These superstructures may be formed through mechanisms such as capillary clumping or by way of application of a polymer coating prior to, during, or following the stacking process.

In some embodiments, a polymer coating and/or adhesive, or other coating as described above, is applied to the CNT array(s) which are subsequently stacked. In such embodiments, the thickness of the coating and/or adhesive, or other coating as described above, is about 1-1000 nm, more preferable 1-500 nm, and most preferably 1-100 nm.

In addition to the above, the favorable deformation mechanics of CNTs present in the multilayered or multitiered structures allow them to efficiently conform to the asperities of adjoining surfaces, resulting in high contact areas at the interfaces.

A. Reduction in Thermal Resistance

The CNT arrays or sheets and the multilayered or multitiered structures formed by stacking of such CNT arrays described herein exhibit reduced thermal resistance. The thermal resistance can be measured using a variety of techniques known in the art, such as the photoacoustic (PA) method.

In one embodiment, the thermal resistance of the CNT arrays or sheets and the multilayered or multitiered structures formed by stacking of such CNT arrays or sheets is reduced by at least about 25%, 30%, 35%, 40%, 45%, 50%, 55%, 60%, 65%, 70% or greater compared to single tiered structures when measured, for example, using the photoacoustic method. In other embodiments, the CNT arrays or sheets and the multilayered or multitiered structures formed by stacking of such CNT arrays or sheets exhibit thermal resistances of less than about 10.0, 9.0, 8.0, 7.0, 6.0, 5.0, 4.5, 4.0, 3.5, 3.0, 2.5, 2.0, 1.5 mm² K/W. In some embodiments, the thermal resistance is about 2, preferably about 1 mm²K/W. In some embodiments, the thermal resistance value of a multilayered or multitiered structures formed by stacking of CNT arrays or sheets is the same or substantially unchanged as compared to the value(s) of the single layer arrays used to form the stack; "substantially," as used herein refers to less than a 10%, 5%, 4%, 3%, 2%, or 1% change.

In some embodiments, the CNT arrays or sheets and the multilayered or multitiered structures formed by stacking of such CNT arrays or sheets exhibit conductance values in the range of about 1-1500 W/m²K, or 5-500 W/m²K.

Applying a coating to the CNT arrays or sheets prior to, during, or following stacking to form multilayered or multitiered structures formed by stacking of such CNT arrays or sheets was shown to be an effective means for increasing the contact area and reducing the thermal resistance of CNT forest thermal interfaces. The bonding process added by inclusion of nanoscale coatings around individual CNT contacts includes, for example, pulling, through capillary action, of additional CNTs close to the interface to increase contact area.

IV. Methods for Preparing CNT Arrays and Multilayered or Multitiered Structures Formed Therefrom A. Carbon Nanotube (CNT) Arrays Carbon nanotube arrays can be prepared using techniques well known in the art. In one embodiment, the arrays are prepared as described in U.S. Publication No. 2014-0015158-A1, incorporated herein by reference. This method involves the use of multilayer substrates to promote the growth of dense vertically aligned CNT arrays and provide excellent adhesion between the CNTs and metal surfaces.

The multilayer substrates contain three or more layers deposited on an inert support, such as a metal surface. Generally, the multilayer substrate contains an adhesion layer, an interface layer, and a catalytic layer, deposited on the surface of an inert support. Generally, the support is formed at least in part from a metal, such as aluminum, platinum, gold, nickel, iron, tin, lead, silver, titanium, indium, copper, or combinations thereof. In certain instances, the support is a metallic foil, such as aluminum or copper foil. The support may also be a surface of a device, such as a conventional heat sink or heat spreader used in heat exchange applications.

The adhesion layer is formed of a material that improves the adhesion of the interface layer to the support. In certain embodiments, the adhesion layer is a thin film of iron. Generally, the adhesion layer must be thick enough to remain a continuous film at the elevated temperatures used to form CNTs. The adhesion layer also generally provides resistance to oxide and carbide formation during CNT synthesis at elevated temperatures.

The interface layer is preferably formed from a metal which is oxidized under conditions of nanotube synthesis or during exposure to air after nanotube synthesis to form a suitable metal oxide. Examples of suitable materials include aluminum. Alternatively, the interface layer may be formed from a metal oxide, such as aluminum oxide or silicon oxide. Generally, the interface layer is thin enough to allow the catalytic layer and the adhesion layer to diffuse across it. In some embodiments wherein the catalytic layer and the adhesion layer have the same composition, this reduces migration of the catalyst into the interface layer, improving the lifetime of the catalyst during nanotube growth.

The catalytic layer is typically a thin film formed from a transition metal that can catalyze the formation of carbon nanotubes via chemical vapor deposition. Examples of suitable materials that can be used to form the catalytic layer include iron, nickel, cobalt, rhodium, palladium, and combinations thereof. In some embodiments, the catalytic layer is formed of iron. The catalytic layer is of appropriate thickness to form catalytic nanoparticles or aggregates under the annealing conditions used during nanotube formation.

In other embodiments, the multilayer substrate serves as a catalytic surface for the growth of a CNT array. In these instances, the process of CNT growth using chemical vapor deposition alters the morphology of the multilayer substrate. Specifically, upon heating, the interface layer is converted to a metal oxide, and forms a layer or partial layer of metal oxide nanoparticles or aggregates deposited on the adhesion layer. The catalytic layer similarly forms a series of catalytic nanoparticles or aggregates deposited on the metal oxide nanoparticles or aggregates. During CNT growth, CNTs form from the catalytic nanoparticles or aggregates. The resulting CNT arrays contain CNTs anchored to an inert support via an adhesion layer, metal oxide nanoparticles or aggregates, and/or catalytic nanoparticles or aggregates.

In particular embodiments, the multilayer substrate is formed from an iron adhesion layer of about 30 nm in thickness, an aluminum or alumina interface layer of about 10 nm in thickness, and an iron catalytic layer of about 3 nm in thickness deposited on a metal surface. In this embodiment, the iron adhesion layer adheres to both the metal surface and the Al (alumina nanoparticles or aggregates after growth) or $Al_2O_3$ interface layer. The iron catalytic layer forms iron nanoparticles or aggregates from which CNTs grow. These iron nanoparticles or aggregates are also bound to the alumina below.

As a result, well bonded interfaces exist on both sides of the oxide interface materials. Of metal/metal oxide interfaces, the iron-alumina interface is known to be one of the strongest in terms of bonding and chemical interaction. Further, metals (e.g., the iron adhesion layer and the metal surface) tend to bond well to each other because of strong electronic coupling. As a consequence, the CNTs are strongly anchored to the metal surface.

Further, subsurface diffusion of iron from the catalytic layer during nanotube growth is reduced because the same metal is on both sides of the oxide support, which balances the concentration gradients that would normally drive diffusion. Therefore, catalyst is not depleted during growth, improving the growth rate, density, and yield of nanotubes in the array.

In some embodiments, the CNT array is formed by vertically aligning a plurality of CNTs on the multilayer substrate described above. This can be accomplished, for example, by transferring an array of CNTs to the distal ends of CNTs grown on the multilayer substrate. In some embodiments, tall CNT arrays are transferred to the distal ends of very short CNTs on the multilayer substrate. This technique improves the bond strength by increasing the surface area for bonding.

The inert support for the CNT array or sheet can be a piece of metal foil, such as aluminum foil. In these cases, CNTs are anchored to a surface of the metal foil via an adhesion layer, metal oxide nanoparticles or aggregates, and catalytic nanoparticles or aggregates. In some instances only one surface (i.e., side) of the metal foil contains an array or sheet of aligned CNTs anchored to the surface. In other cases, both surfaces (i.e., sides) of the metal foil contain an array or sheet of aligned CNTs anchored to the surface. In other embodiments, the inert support for the CNT array or sheet is a surface of a conventional metal heat sink or heat spreader. In these cases, CNTs are anchored to a surface of the heat sink or heat spreader via an adhesion layer, metal oxide nanoparticles or aggregates, and catalytic nanoparticles or aggregates. This functionalized heat sink or heat spreader may then be abutted or adhered to a heat source, such as an integrated circuit package.

B. Carbon Nanotube Sheets

Carbon nanotube sheets can be prepared using techniques well known in the art. In one embodiment, the sheets are prepared as described in U.S. Pat. No. 7,993,620 B2. In this embodiment, CNT agglomerates are collected into sheets in-situ inside the growth chamber on metal foil substrates. The sheets can then be densified by removing the solvent. In another embodiment, the CNT sheets are made by vacuum filtration of CNT agglomerates that are dispersed in a solvent.

C. Coated Nanotube Arrays and Sheets

1. Polymer Coatings

Polymers to be coated can be dissolved in one or more solvents and spray or dip coated or chemically or electrochemically deposited onto the vertical CNT forests or arrays grown on a substrate, or on a sheet, as described above. The coating materials can also be spray or powder coated onto the vertical CNT forests or arrays grown on a substrate, or on CNT sheets as described above. The coatings includes polymers or molecules that bond to CNTs through van der Waals bonds, π-π stacking, mechanical wrapping and/or covalent bonds and bond to metal, metal oxide, or semiconductor material surfaces through van der Waals bonds, π-π stacking, and/or covalent bonds.

For spray or dip coating, coating solutions can be prepared by sonicating or stirring the coating materials for a suitable amount of time in an appropriate solvent. The solvent is typically an organic solvent or solvent and should be a solvent that is easily removed, for example by evaporation at room temperature or elevated temperature. Suitable solvents include, but are not limited to, chloroform. The polymer can also be spray coated in dry form using powders with micron scale particle sizes, i.e., particles with diameters less than about 100, 50, 40, 20, 10 micrometers. In this embodiment, the polymer powder would need to be soaked with solvent or heated into a liquid melt to spread the powder particles into a more continuous coating after they are spray deposited.

The thickness of the coatings is generally between 1 and 1000 nm, preferably between 1 and 500 nm, more preferably between 1 and 100 nm, most preferably between 1 and 50 nm. In some embodiments, the coating thickness is less than 500, 450, 400, 350, 300, 250, 200, 150, 100, 90, 80, 70, 60, 50, 40, 30, 20 or 10 nm. The coatings may be conformally applied to the tips of the CNTs and/or vertical walls of the CNTs of the arrays.

Spray coating process restricts the deposition of coating to the CNT tips and limits clumping due to capillary forces associated with the drying of the solvent. The amount of coating visible on the CNT arrays increases with the number of sprays. Alternative techniques can be used to spray coat the coating materials onto the CNT arrays including techniques more suitable for coating on a commercial scale.

In another embodiment that demonstrates a coating process, CNT sheets are dipped into coating solutions or melted coatings to coat CNTs throughout the thickness of the sheets, increasing the thermal conductivity of the sheet in the cross-plane direction by greater than 20, 30, 50, or 70%. These coated sheets are then placed between a chip and heat sink or heat spreader with the application of solvent or heat to reflow the polymer and bond the CNT sheet between the chip and heat sink or spreader to reduce the thermal resistance between the chip and heat sink or heat spreader.

In other embodiments, the coating material can be deposited on the CNT array or sheet using deposition techniques known in the art, such as chemical deposition (e.g., chemical vapor deposition (CVD)), aerosol spray deposition, and electrochemical deposition. Powder coating may also be used to apply (conformal) coatings of polymeric materials which are typically micronized polymeric materials of a suitable average particle size (i.e., less than about 10,000 microns to 1 micron, 1 micron to 1 nm, or any range disclosed therein). Without limitation, a micronized powder may be applied using a powder coating gun which provides a motive force by electrically charging the micronized polymeric material (i.e., particles) up to about 30 kV, 25 kV, 20 kV, 15 kV, 10 kV, or 5 kV and applying the charged particles to vertically aligned CNTs on a substrate or stacks formed therefrom, where the substrate(s) and CNTs are grounded. Following application of one or more powder coatings, the coating may be heated by any conventional means to melt, set, and/or cure the polymeric coating(s). Powder coatings may be repeated one or more times, as appropriate.

In some embodiments, a polymer coating can be applied by electrochemical deposition. In electrochemical deposition, the monomer of the polymer is dissolved in electrolyte and the CNT array or sheet is used as the working electrode, which is opposite the counter electrode. A potential is applied between the working and counter electrode with respect to a third reference electrode. The monomer is electrooxidized on the CNT array tips or sheet sidewalls that face the electrolyte as a result of the applied potential. Controlling the total time in which the potential is applied controls the thickness of the deposited polymer layer.

In some embodiments, the coating material is, or contains, one or more oligomeric and/or polymeric materials. In particular embodiments, the polymer can be a conjugated polymer, including aromatic and non-aromatic conjugated polymers. Suitable classes of conjugated polymers include polyaromatic and polyheteroaromatics including, but not limited to, polythiophenes (including alkyl-substituted polythiophenes), polystyrenes, polypyrroles, polyacetylenes, polyanilines, polyfluorenes, polyphenylenes, polypyrenes, polyazulenes, polynaphthalenes, polycarbazoles, polyindoles, polyazepines, poly(3,4-ethylenedioxythiophenes), poly(p-phenyl sulfides), and poly(p-phenylene vinylene). Suitable non-aromatic polymers include, but are not limited to, polyacetylenes and polydiacetylenes. The polymer classes listed above include substituted polymers, wherein the polymer backbone is substituted with one or more functional groups, such as alkyl groups. In some embodiments, the polymer is polystyrene (PS). In other embodiments, the polymer is poly(3-hexythiophene) (P3HT).

In other embodiments, the polymer is a non-conjugated polymer. Suitable non-conjugated include, but are not limited to, polyvinyl alcohols (PVA), poly(methyl methacrylates) (PMMA), polydimethylsiloxanes (PDMS), and combinations (blends) thereof. In other embodiments, the polymer is a paraffin wax. In other embodiments, the polymer is a synthetic wax such as Fischer-Tropsch waxes or polyethylene waxes. In other embodiments, the polymer is a wax that has a melting temperature above 80, 90, 100, 110, and 120° C., preferably above 130° C. In other embodiments, the polymer is a hot glue or hot melt adhesive that combines wax, tackifiers and a polymer base to provide improved surface adhesion. In other embodiments, the polymer is a pressure sensitive adhesive.

2. Metallic Nanoparticles

The CNT arrays or sheets can be coated with one or more metal nanoparticles. One or more metal nanoparticles may be adsorbed to the distal ends and/or sidewalls of the CNTs to bond the distal ends of the CNTs to a surface, reduce thermal resistance between the CNT array or sheet and a surface, or combinations thereof. Metal nanoparticles can be applied to CNT arrays or sheets using a variety of methods known in the art. For example, a solution of metal thiolate such as palladium hexadecanethiolate can be sprayed or spin coated onto the distal ends and/or sidewalls of the CNTs, and the organics can be baked off to leave palladium nanoparticles. In another example, electron-beam or sputter deposition can be used to coat metal nanoparticles or connected "film-like" assemblies of nanoparticles onto the distal ends and/or sidewalls of the CNTs. The metallic particles can be coated simultaneously with the coating or before or after coating.

Examples of suitable metal nanoparticles include palladium, gold, silver, titanium, iron, nickel, copper, and combinations thereof.

3. Flowable or Phase Change Materials

In certain embodiments, flowable or phase change materials can be applied to the CNT array or sheet. Flowable or phase change materials may be added to the CNT array or sheet to displace the air between CNTs and improve contact between the distal ends of CNTs and a surface, and as a result reduce thermal resistance of the array or sheet and the contact between the array or sheet and a surface, or combinations thereof. Flowable or phase change materials can be applied to CNT arrays or sheets using a variety of methods known in the art. For example, flowable or phase change materials in their liquid state can be wicked into a CNT array or sheet by placing the array or sheet in partial or full contact with the liquid.

Examples of suitable flowable or phase change materials include paraffin waxes, polyethylene waxes, hydrocarbon-based waxes in general, and blends thereof. Other examples of suitable flowable or phase change materials that are neither wax nor polymeric include liquid metals, oils, organic-inorganic and inorganic-inorganic eutectics, and blends thereof. In some embodiments, the coating material(s) and the flowable or phase change material are the same.

The coatings, metallic particles, and/or flow or phase change materials described above can be applied directly to the CNT arrays or sheets to form coated arrays having CNTs on one or more surfaces of a substrate. Coated CNT arrays or sheets can subsequently be stacked to form multilayered or multitiered structures. In certain other embodiments, the coatings, metallic particles, and/or flow or phase change materials described above are applied during the stacking of two or more CNT arrays or sheets. In still other embodiments, the coatings, metallic particles, and/or flow or phase change materials described above are applied following the stacking of two or more CNT arrays or sheets. In non-limiting embodiments, multilayered or multitiered structure(s) are formed by first stacking two or more CNT arrays or sheets and then the at least partially interdigitated tiers of the formed structures are infiltrated with one or more coatings, metallic particles, and/or flow or phase change materials, or combinations thereof. The introduction of such coatings/materials into the at least partially interdigitated tiers of the multilayered or multitiered structure(s) prior to, during, or after stacking can be used to modify and/or enhance the thermal transport or thermal resistance properties of the multilayered or multitiered structures resulting from the stacking of the CNT arrays or sheets.

D. Multilayered or Multitiered Structures

In the embodiments described herein, single substrates can have one or more CNT arrays formed on surfaces of the substrate and the CNT arrays may be coated as described above.

In other embodiments, multilayered or multitiered structures are formed by stacking CNT arrays or sheets formed by a method including the steps of:

(1) providing at least two or more CNT arrays or sheets; and (2) stacking the at least CNT arrays or sheets wherein the stacking results in at least partial interdigitation of the nanostructures, CNTs, of the arrays or sheets. In some embodiments, the method of making the multilayered or multitiered structures further includes a step of applying or infiltrating a coating, a coating of metallic nanoparticles, and/or a coating of flowable or phase change materials, which are described above. In some embodiments, the step of applying or infiltrating a coating, a coating of metallic nanoparticles, and/or a coating of flowable or phase change materials occurs prior to stacking, alternatively during stacking, or alternatively after stacking. In yet other embodiments, the method includes applying pressure during the stacking step. The applied pressure may be in the range of about 1-30 psi, more preferably about 1-20 psi, and most preferably about 1-15 psi. In some embodiments, the pressure is about 15 psi. Pressure may be applied continuously until the adjacent tiers are bonded, if a coating material(s) which can act as a bonding agent, such as an adhesive or phase change material, is used. Pressure may be applied for any suitable amount of time. In some embodiments, only a short time is used, such as less than 1 minute, if no bonding agent is used.

At least two CNT arrays or sheets can be stacked to form the multilayered or multitiered structures. For example, FIG. 2 shows stacking of three CNT arrays (right side). By using more CNT arrays the thickness of the multilayered or multitiered structures can be increased as needed. In some embodiments, up to 5, 10, 15, 20, 25, 30, or more CNT arrays or sheets can be stacked according to the method described above. The thickness of the resulting multilayered or multitiered structures formed by stacking can be in the range 1-10,000 microns or more.

In a non-limiting embodiment, at least two vertically aligned arrays or sheets formed on supports/substrates are stacked/contacted such that the nanostructure elements, such as CNTs, of the arrays at least partially interdigitate on contact. In one embodiment full interdigitation of nanostructure elements of the arrays occurs within one another when stacked. In other embodiments the arrays may interdigitate only at the tips of the nanostructure elements, such as CNTs. In yet other embodiments, the individual nanostructures can navigate through the nanostructures of the adjacent array during the interdigitating process.

In some embodiments the nanostructures of the stacked arrays, which interdigitate at least partially, may also form into larger superstructures, such as, but not limited to, tube bundles, clumps, or rows. These superstructures may be formed through mechanisms such as capillary clumping or by way of application of a polymer coating prior to, during, or following the stacking process.

In some embodiments, a polymer coating and/or adhesive, or other coating as described above, is applied to the CNT array(s) which are then stacked. In such embodiments, the thickness of the coating and/or adhesive, or other coating as described above, is about 1-1000 nm, more preferable 1-500 nm, and most preferably 1-100 nm.

V. Applications

Single-layer substrates having one or more coated CNT arrays thereon, or multilayered or multitiered structures formed therefrom by stacking of CNT arrays or sheets described herein can be used as thermal interface materials (TIMs). The multilayered or multitiered structures formed by stacking of CNT arrays or sheets can be formed and/or deposited, as required for a particular application.

The single-layered CNT arrays and multilayered or multitiered structures formed by stacking of such CNT arrays described herein can be used as thermal interface materials (TIMs) in personal computers, server computers, memory modules, graphics chips, radar and radio-frequency (RF) devices, disc drives, displays, including light-emitting diode (LED) displays, lighting systems, automotive control units, power-electronics, solar cells, batteries, communications equipment, such as cellular phones, thermoelectric generators, and imaging equipment, including MRIs.

In certain embodiments, the single-layered or multilayered or multitiered structures formed by stacking of CNT arrays are useful in low contact pressure and/or low pressure applications. Low pressure may refer to ambient pressure or pressures below 1 atm, such as in the range of about 0.01 to less than about 1 atm. In some instances, low pressure may refer to a vacuum such as in aerospace applications where such TIMs could be used in satellites or space vehicles/systems.

In certain embodiments, the multilayered or multitiered structures formed by stacking of CNT arrays are useful at temperatures which are below ambient temperature, below freezing, or at cryogenic temperatures (such as experienced in space).

The CNT arrays and the multilayered or multitiered structures formed by stacking of such CNT arrays described herein can also be used for applications other than heat transfer. Examples include, but are not limited to, microelectronics, through-wafer vertical interconnect assemblies, and electrodes for batteries and capacitors. Currently, copper and aluminum foil are used as the backing materials for the anode and cathode in lithium ion batteries.

The single-layered or multilayered or multitiered structures formed therefrom by stacking can also be used for electromagnetic shielding.

A. Burn-In and Thermal Applications

One highly specialized and under developed application for TIMs involves burn-in and test applications. Integrated circuit manufacturers attempt to induce eventual failure during an infant mortality period through a combination of "burn-in" and stress testing on their chips. In burn-in testing, chips are exercised at elevated temperatures taking advantage of the inverse relationship between reliability and operating temperature (A. Vassighi, O. Semenov, M. Sachdev, and A. Keshavarzi, "Thermal Management of High Performance Microprocessors," in null, 2003, p. 313). Because devices are being exercised at their performance limits during testing, an effective thermal interface material (TIM) is essential. The desired characteristics of TIMs for burn in applications are: low thermal resistance, high mechanical compliance, high robustness, and leaving no residue on the chips (N. F. Dean and A. Gupta, "Characterization of a thermal interface material for burn-in application," in *Thermal and Thermomechanical Phenomena in Electronic Systems*, 2000. *ITHERM* 2000. *The Seventh Intersociety Conference on,* 2000).

Accordingly, TIM materials are well suited for applications where repeated cycling is required. For example, they can be employed as thermal interface materials during 'burn-in' testing of electrical components, such as chips. In some embodiments, the inert support/substrate of the CNT arrays described herein can be one or more surfaces of a conventional metal heat sink or a spreader. This functionalized heat sink or spreader may then be abutted or adhered to a heat source, such as an integrated circuit package. Such TIM materials can also be placed or affixed in between a heat source and a heat sink or heat spreader, such as between an integrated circuit package and a finned heat exchanger, to improve the transfer of heat from the heat source to the heat sink or spreader.

The single-layered and/or multilayered or multitiered stacks described herein can be used for TIM applications, such as but not limited to burn-in testing.

In some embodiments, the method can involving using single-layer CNT composites and multilayered or multitiered structures formed therefrom described herein in testing involving pressure, heating, electrical, or a combination. Generally, contact is made to the device under test with a thermally conductive and/or electrically conductive, mechanically compliant substrate having an adhesive surface. In some embodiments, the method can include the steps of:

engaging a thermal or electrical unit head with a substrate attached directly to the unit head with a pressure of at least 10 psi and engagement temperature less than 150° C.;

holding the engagement under the pressure of at least 10 psi for at least 5 minutes or cycling the engagement at least one to five times, wherein during each engagement the device under test is powering up and heating the thermal or electrical unit head to simulate the device powering up to reach a temperature of at least 50° C.; and disengaging and re-engaging the thermal or electrical head and substrate with the device under test for at least 1,500 cycles of powering up.

The method can involve or result in testing the device under test in order to determine the thermal resistance and/or relative thermal resistance following cycling.

In certain embodiments, single-layer CNT composites and multilayered or multitiered structures formed therefrom described herein are used in a method for making contact to a device under test with a thermally conductive and/or electrically conductive, mechanically compliant substrate having an adhesive surface, the method comprising the steps of:

(1) attaching the substrate directly to a thermal or electrical unit head to cover the area of the head completely or matching the size of the device under test;

(2) engaging the thermal or electrical unit head with the attached substrate to the device under test with a pressure of at least 10 psi and engagement temperature less than 150° C.;

(3) holding the engagement under the pressure of at least 10 psi for at least 5 minutes or cycling the engagement at least one to five times, wherein during each engagement the device under test is powering up and heating the thermal or electrical unit head to simulate the device powering up to reach a temperature of at least 50° C.;

(4) disengaging and re-engaging the thermal or electrical head and substrate with the device under test for at least 1,500 cycles of powering up; and (5) testing the device under test; in order to determine the thermal resistance and/or relative thermal resistance following cycling.

In the methods described the engagement pressure is at least 10 psi. The engagement pressure can be in the range of between about 10 psi to 300 psi, 10 psi to 250 psi, 10 psi to 200 psi, 10 psi to 175 psi, or ranges disclosed therein.

In the methods described the number of engagement cycles may be at least 1 to 5, 5 to 1,000, 5 to 5,000, or 10,000 to 100,000 engagement cycles which are preferably performed without removing the substrate or without having to clean any debris or marks from the device under test.

In the methods described the engagement cycles (i.e., engaging, disengaging, and re-engaging) may each independently be carried out for any suitable period of time. Each cycle may independently occur for at least 1 second to 300 seconds, 1 second to 250 seconds, 10 seconds to 200 seconds, 10 seconds to 180 seconds, 20 seconds to 180 seconds, 30 seconds to 180 seconds, and ranges disclosed therein.

In the methods described the device under test is tested at a temperature of between about −55° C. to 140° C., −50° C. to 130° C., −40° C. to 120° C., −30° C. to 110° C., −20° C. to 100° C., −10° C. to 90° C., 0° C. to 80° C., and 10° C. to 70° C., or temperature ranges disclosed therein.

In the methods described the surface of the substrate can be treated or modified in order to prevent mechanical sticking between the unit head and the device under test, which can prevents stress generation in the device and prevents the device from being pulled from the test socket.

In the methods described the substrate can make contact to between 1 to 100 dies, 1 to 50 dies, 1 to 25 dies, 1 to 15 dies, or 1 to 10 dies, i.e., multi-die or multi-chip testing, present on the same substrate, at the same time, and wherein the dies can be of different heights, shapes, and/or sizes.

In the methods described the substrate can be attached to the device under test and is not attached to the thermal or electrical unit head.

In the methods described the substrate can be precision cut to dimensions of a device under test, or to dimensions of the thermal or electrical unit head and allows for penetration through the substrate of one or more sensors, one or more mounting alignment pins, one or more vacuum chuckings, or combinations thereof.

In the methods described the substrate when applied or installed onto a pedestal or to the thermal or electrical unit head can be removed from the pedestal, thermal or electrical unit head without leaving any adhesive residue or substantially any adhesive residue ("substantially any residue" refers to less than 10%, 9%, 8%, 7%, 6%, 5%, 4%, 3%, 2%, 1%, 0.9%, 0.8%, 0.7%, 0.6%, 0.5%, 0.4%, 0.3%, 0.2%, or 0.1% by weight of total adhesive present on the substrate initially). In such instances, where no residue remains there is no requirement for scraping of the pedestal, thermal or electrical unit head when removal occurs. In instances, where substantially no residue remains only minimal scraping (or substantially no scraping) of the pedestal, thermal or electrical unit head may be needed when removal occurs.

In the methods described the substrate can be attached to the device under test and is not attached to the thermal or electrical unit heat and the substrate remains attached to the device under test following completion of the testing step in order to be packaged with the device in its subsequent forms for further testing or packaging for sale.

In the methods described the substrate adds between about 0.01 and 3.0 cm² K/W, 0.05 and 2.0 cm² K/W, 0.05 and 1.5 cm² K/W, 0.05 and 1.0 cm² K/W, 0.05 and 0.5 cm² K/W, 0.05 and 0.1 cm² K/W and ranges disclosed within of thermal resistance, as determined following the testing step.

In the methods described the substrate has an in-plane thermal conductivity that is between about 100 and 2,000 W/m K, 100 and 1,900 W/m K, 100 and 1,800 W/m K, or 100 and 1,700 W/m K, and ranges disclosed therein in order to spread heat from local hot spots on the device under test.

In the methods described the substrate has a low thermal mass (i.e., ability to absorb and store heat energy) and thermal conductivity through a plane which is greater than 1, 2, 3, 4, 5, 6, 7, or 8 W/m K and the time required to test the device under test is minimal, that is less than 10 min, less than 5 min, less than 3 min, less than 1 min, less than 30 seconds.

In the methods described the substrate preferably only adds between 0.001 and 10 Ohms for 1 cm$^2$ to the testing step.

In the methods described the substrate can be used to short circuit an array of electrical contact pins for characterization of the electrical contacts.

In the methods described the substrate preferably has a compression set of less than 5 microns.

In the methods described the substrate can preferably be compressed to at least 5% of its original thickness with an applied pressure of less than 100 psi.

In the methods described the substrate can be compressed by as much as 50% of its original thickness preferably without tearing or shear failure.

In the methods described the substrate can be compressed to different amounts in different areas of the substrate, while maintaining surface contact to 1 or more dies or chips, having different sizes, shapes, or heights, on the same board.

In the methods described the adhesive is preferably a thermoplastic or pressure sensitive adhesive that is present, applied to, or imbedded on or in the surface layer of the substrate and which preferably does not add more than 5 microns of adhesive thickness between the substrate and contact surface while maintaining strong mechanical bonding properties. The adhesive may be any suitable commercial adhesive or combination of adhesives, which are preferably low resistance adhesive(s). The adhesive may also be formed from one or more coating materials, such as a polymer, or combinations thereof described herein with respect to the CNT arrays on a substrate. The adhesive preferably renders the TIM material a "peel-and-stick" TIM material, which can readily be placed and adhered when a suitable release liner is peeled off the adhesive side of the TIM material.

In the methods described the thermal unit may be a part of an automatic test equipment (ATE) pick and place handler and the substrate can replace the need for a pedestal or a device kit for different device shapes or geometries.

In the methods described the substrate can be applied to a pedestal or to the thermal or electrical unit head prior to installation of the pedestal or the thermal or the electrical unit head to an automatic test equipment (ATE) pick and place handler, a burn-in oven, or other such test equipment which may be used for the same or similar purposes.

In the methods described the thermal unit can be a part of a burn-in oven and the substrate can replace the need for a pedestal or device kit for different device shapes or geometries.

In the methods described the substrate can be used in combination with a metal pedestal on one or both sides of a pedestal.

In the methods described the compliant substrate can replace the need for a liquid to be inserted during each test engagement cycle or used in combination with liquid that enhances performance.

In the methods described the mechanically compliant substrate can minimize the need to polish mating surfaces to a factory mill finish (as determined by industry standards) or to a greater degree than a factory mill finish.

In the methods described the substrate is preferably between about 10 to 10,000 micrometers in thickness.

In the methods described the substrate is preferably less than about 100 microns in thickness and does not tear or degrade from an applied shear force during head contact to the device under test.

In the methods described the substrate can deform to fill a gap between the device under test and the thermal or electrical unit head when the center to edge curvature of the device or head is preferably between about 5-200 microns or a range disclosed therein.

In the methods described the substrate is a vertically aligned carbon nanotube array grown on one or both sides of a metal or graphite foil or sheet.

In the methods described the substrate can be a multilayer stack of vertically aligned carbon nanotube array grown on one or both sides of a metal, such as aluminum, or graphite foil or sheet, wherein the number of layers is between 1 to 20, 1 to 15, 1 to 10, 1 to 5, 1 to 3, or 1 to 2.

In the methods described the substrate may be a flexible glass or ceramic or a dielectric foil or sheet, or a metal foil coated with a dielectric layer that provides electrical isolation.

In the methods described the substrate is a vertically aligned carbon nanotube array formed using a catalyst anchored to the substrate. Methods of forming such vertically aligned carbon nanotube array are described in detail in U.S. application Ser. Nos. 13/546,827 and 14/414,227 which are incorporated herein in relevant part by reference.

In the methods described the substrate can be attached permanently or semi-permanently to either the heat source or the heat sink through the use of a conformal coating of thermoplastic adhesive, where the addition of the thermoplastic adhesive does not increase thermal resistance of the substrate, as compared to the substrate without adhesive. Any suitable commercial thermoplastic adhesive or combination of adhesives may be used. The adhesive may also be formed from one or more coating materials, such as a polymer, or combinations thereof described herein with respect to the CNT arrays on a substrate. The adhesive preferably renders the TIM material a "peel-and-stick" TIM material, which can readily be placed and adhered when a suitable release liner is peeled off the adhesive side of the TIM material.

In the methods described the adhesives described which are used on the TIM material leave no residue or leave minimal residue after removal. Minimal residue refers to less than 5%, 4%, 3%, 2%, or 1% by weight of any residual material after the TIM is removed. Any residue remaining may be cleaned with low toxicity solvents, such as but not limited to isopropyl alcohol or water. In the methods described the substrate is a carbon nanotube array on a metal substrate or a multilayer stack thereof, as described above, that is infiltrated or coated with one or more polymers, where the polymer coating is coplanar and/or conformal with the CNT tips and/or CNT walls; or has no more than about 100 nm, 200 nm, 300 nm, 400 nm, 500 nm, 750 nm, or 1000 nm of excess polymer above the CNT tips. Preferably the polymer(s) are durable, low compression set polymers. Preferably the polymer does not or substantially does not weep, sweat, evaporate, or otherwise transfer residue to the device under test. "Substantially," as used herein in refers to less than 10%, 5%, 4%, 3%, 2%, or 1% weeping, sweating, evaporating, or otherwise transferring of residue to the device under test. Preferably the polymer(s) has a high dielectric strength with high electrical resistivity.

In the methods described the CNT tips of the arrays of the TIMS remain available to make electrical contact with a surface that it is intended to mate with, such as the device or a subsection or component thereof.

In the methods described the adhesives described do not add thermal or electrical resistance to the substrate interfacing with the device under test or the thermal/electrical contact head.

In the methods described the adhesive is preferably a peel and stick adhesive and/or thermally activated adhesive. Suitable adhesives are known in the art.

In the methods described the device can be tested without removing the substrate or having to clean debris or marks from the device under test.

In the methods described the substrate is preferably a coated CNT array thermal interface material (TIM). In certain embodiments the coated CNT array TIM is a single layered TIM having one or both surfaces of a substrate having coated CNT forests thereon. In some embodiments, the coating is a polymer coating which is preferably a polyethylene wax wherein the wax coating is a uniform and conformal coating present on the CNT tips and/or CNT walls of the array. The coating is preferably applied by a powder coating deposition method, as described above.

In certain other embodiments the coated CNT array-based TIM are formed from multiple single layered TIM having one or both surfaces of a substrate having coated CNT forests thereon. The multilayered stacks are described herein. In some embodiments, the coating is a polymer coating which is preferably a polyethylene wax wherein the wax coating is a uniform and conformal coating present on the CNT tips and/or CNT walls of the array. The coating is preferably applied by a powder coating deposition method, as described above.

The single-layered and/or multilayered or multitiered stacks CNT arrays described herein can also be incorporated into systems, devices, and/or apparatuses for temperature control of electronic devices, such as but not limited to thermal controllers. Such systems, devices, and/or apparatuses are described, for example, in U.S. Pat. Nos. 6,489,793, 6,636,062, and 8,896,335 which are incorporated in relevant part by reference.

B. Thermal Interface Material Kits

The coated CNT array-based TIM materials (also denoted CNT-TIM composites) described herein can be used in a variety of applications, including but not limited to military, industrial manufacturing, and automotive manufacturing.

As a non-limiting example, the CNT-TIM composites may be prepared according to the methods described herein and provided as a kit.

Kits may include one or more of the CNT-TIM composites described. Preferably the CNT-TIM composite is an adhesive peel-and-stick TIM material. The kit may further include a suitable amount of an alcohol (such as isopropyl alcohol (IPA)) in a container, a lint free cloth, protective gloves, and tweezers.

The kit also includes instructions detailing the preparation of the substrate to which the CNT-TIM composite is to be applied to and detailed application instructions. For example, surface preparation may include wearing protective gloves and cleaning the surface (such as a heat sink) using IPA and a lint-free cloth. In one embodiment the application instructions include the steps of:

Wearing protective gloves and using tweezers to remove a release liner from the peel-and-stick CNT-TIM composite material ensuring that one does not touch the adhesive prior to application. While the adhesive has a long open time, it should be applied quickly after the release liner is removed to avoid any particle or other environmental contamination; and Attaching the released peel-and-stick CNT-TIM composite to a substrate, such as a heat sink head, preferably beginning from one end of the substrate and working towards the opposite end of the substrate to ensure the CNT-TIM composite is flat to the surface. Pressure should be applied normal to the applied CNT-TIM composite and no pressure should be applied, such as by sliding fingers across the applied CNT-TIM composite.

Figure 10:
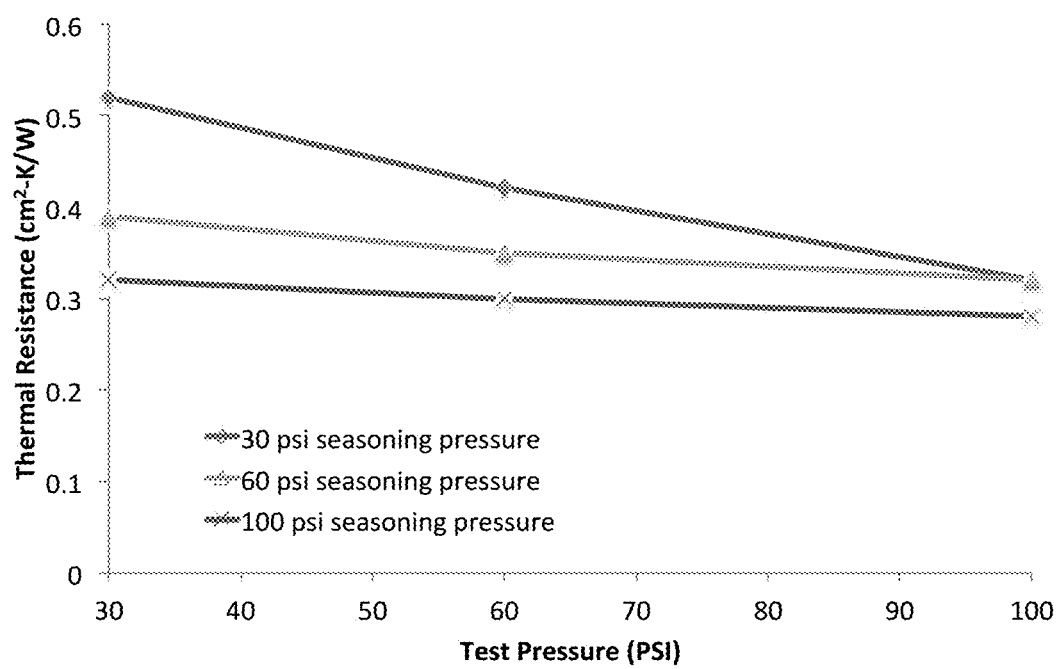
FIG. 10 shows a graph of the thermal resistance versus applied pressure of CNT-TIM composites at 30 psi, 60 psi, and 100 psi.

The applied CNT-TIM composite may further be seasoned according to instructions detailing the following steps:

Applying a pressure of at least 10, 20, or 30 psi at an engagement temperature which is preferably below 50° C. The pressure applied during seasoning may be as high as 200 psi, 150 psi, 100 psi, or 75 psi. Using higher pressures can result in improved thermal resistance properties of the CNT-TIM composites (see FIG. 10)

Heating the substrate, such as a heat sink, on the side of the applied CNT-TIM composite to a temperature of about 90° to 120° C., preferably to at least about 110° C.

Holding the composite under pressure at the appropriate temperature for about 1 to 30 minutes, 1 to 20 minutes, 1 to 10 minutes, 5 to 10 minutes, and more preferably at least about 8 minutes.

Allowing the substrate, such as a heat sink, to cool to a temperature below 75° C., 60° C., 50° C., 40° C., or 30° C.; and Disengaging the substrate, such as a heat sink, from the applied pressure.

The seasoning steps may be repeated, as necessary.

The kit also include warnings about avoiding touching the pressure sensitive adhesive and introducing crease marks and/or bubbles prior to, during, or following installation or seasoning of the CNT-TIM composite.

The kit can also include instructions for removal of the CNT-TIM composite. For example, if the CNT-TIM composite was seasoned then removal includes the steps of:

Using tweezers and protective gloves,

Grabbing the CNT-TIM composite from a corner and peeling off, and

Cleaning any residue from the substrate, such as a heat sink, surface using IPA and a lint free cloth.

If the CNT-TIM composite was not seasoned then removal includes the step of:

Peeling off the CNT-TIM composite;

Cleaning any residue from the substrate, such as a heat sink, surface using IPA and a lint free cloth.

In certain other embodiments, the thermal interface material kit as described above may be provided as a part of a larger device changeover kit intended to prepare an automatic test equipment (ATE) handler, a burn in oven, or other such test system used to accept a new product for testing. Typical items included in a device changeover kit may include, but are not limited to, pedestals designed to match the dimensions of the new product, new sockets, and other such accessories.

In another embodiment, the thermal interface material kit as described above can be supplied as an additional accessory in a device changeover kit, as described above, along with installation instructions and related materials.

In yet another embodiment, the thermal interface materials described may be applied to one or more surfaces of a component present in a kit (e.g. a pedestal surface, or other mating surface(s) of one or more components or parts within a device changeover kit). In such an embodiment, installation instructions and materials may be optionally included, as the thermal interface materials are pre-applied to the one or more surfaces of component(s) present in the kit, such as prior to delivery to an end-user.

EXAMPLES

Example 1: Multilayered/Multitiered CNT-Based Thermal Interface Materials (TIMs)

Methods:

Thermal Measurement System Design:

Heat transfer properties for all test specimens were evaluated using a test fixture designed and built based on the methods described in ASTM D5470 "Standard Test Method for Thermal Transmission Properties of Thermally Conductive Electrical Insulation Materials." It not only allows for deformation of the test specimens but also incorporates a vacuum chamber to minimize conductive and convective heat losses. A schematic diagram of the fixture design is shown in FIG. 1. The vacuum chamber was constructed of stainless steel with an acrylic door, and is capable of maintaining vacuum in the $10^{-5}$ torr range. The vacuum chamber sits on the reaction plate of a 1000 lb load frame, with all feedthroughs near the top of the chamber. Thermocouples were fed via a pair of Omega 4-pair feedthroughs (8 thermocouples possible). The cooling tubes possess bulkhead fittings with o-ring seals. The power for the heaters was controlled via a Watlow SD controller with a thermocouple feedback loop. The heating block was surrounded by an FR 4 fiberglass insulator shell and the cooling block sits atop a fiberglass insulative plate with machined recessed sections to maintain centrality with the heating block. Both 1"×1" and 4"×4" heating blocks and cooling blocks were fabricated to accommodate planned testing for this program.

Heat Transfer Coefficient Evaluation:

Heat transfer evaluations were conducted with a 20° C. differential between the hot and cold meter blocks of the test fixture. It was found that a temperature differential as close as possible to 20° C. was required to drive heat transfer in the system such that accurate results could be obtained. Test data were imported directly from the data output file of the test, which was acquired via LabView. The Thermal Conductivity ($\lambda$) of the meter bars (5005 series Aluminum) was calculated for the specific temperature using the algorithm for aluminum from NIST (E. Marquardt, J. Le, and R. Radebaugh, "Cryogenic Material Properties Database Cryogenic Material Properties Database," 2000).

Heat flow through each individual meter bar was then calculated from Equation 1:

$$Q = (\lambda A/d)(\delta T) \tag{1}$$

where Q is the heat flow through the bar, A is cross sectional area, d is the distance between thermocouples and $\delta T$ is the difference in temperature from one thermocouple to the other in Kelvin. The values for the hot and cold meter blocks were then averaged to gain $Q_{TOTAL}$. Thermal impedance in $m^2 K/W$ was then evaluated through Equation 2:

$$\theta = (A/Q_{AVG})*\delta T \tag{2}$$

where $\delta T = T_H - T_C$ is the difference between the specific temperatures at the interface of the evaluated material and the meter blocks, A is the cross sectional area of the material, and Q is the average heat flow through the meter blocks.

Thermal conductivity was then calculated using Equation 3:

$$\lambda = Q_{AVG}*\delta d/A*\delta T \tag{3}$$

where $\delta d$ is the change in thickness of the specimen, A is cross sectional area of the specimen and $\delta T$ is the temperature difference across the specimen in Kelvin.

The heat transfer coefficient of the test specimens was calculated via Equation 4:

$$c = Q_{AVG}/A*\delta T \tag{4}$$

Sample Fabrication:

CNT arrays were grown on both aluminum (Al) and copper (Cu) substrates using an iron catalyst to evaluate their differences in performance. CNT growth was performed using a low-pressure chemical vapor deposition (LPCVD) process.

Three different CNT height-foil combinations were tested:

Series #1-50 micron Al substrate with 50 micron nanotubes on each side

Series #2-50 micron Al substrate with 75 micron nanotubes on each side

Series #3-50 micron copper substrate with 150 micron nanotubes on each side

In general, the nanotube quality was very good for all lengths fabricated. However as the tube length increased, the presence of defects also increased. Furthermore, the ultimate achievable height of the CNTs was limited by back diffusion of the catalyst into the substrate and diffusion of the substrate into the catalyst stack. For applications where thicker samples with more compliance were required, an increased height of the TIM was achieved by stacking double-sided forests/arrays, as shown schematically in FIG. 2.

Two different stack configurations utilizing single TIMs on aluminum (Al) substrates were evaluated. The first configuration, denoted "dry" stack, was assembled from three individual TIMs and then evaluated as prepared. The second stack configuration involved bonding the individual TIMs together at the tube-to-tube interfaces using a very thin sprayed on wax material. These sprayed-on interface materials have been shown to dramatically decrease thermal resistance in CNT-based thermal interface materials. The maximum usable temperature for the synthetic wax is 150° C., well within the expected operating range of these TIMs and the very thin layers (~100 nm) employed are not expected to present any outgassing issues.

All initial evaluations were conducted at ambient pressure with an average temperature of 50° C. and a temperature differential of 20° C. between the heated and cooled meter blocks in the test fixture. Once the thermal performance of the first and second configuration TIM stacks had been verified at ambient pressure, additional testing was conducted under vacuum. A median temperature of 50° C. and a temperature differential of 20° C. were used to enable comparison with ambient pressure data.

Results and Discussion:

Dry Stacks:

Actual displacements measured with the instrument crosshead ranged from 430 µm to 480 µm with an applied pressure of 10 kPa (1.5 psi) and from 355 µm to 460 µm with an applied pressure of 69 kPa (10 psi). This suggested some combination of CNT buckling and/or interface interdigitation. It is noted that the displacement measurement is not the same as a true thickness in that it can be difficult to discern exactly the point at which contact to the TIM stack is made for the displacement measurement. CNT buckling and interdigitation of adjacent CNT layers must also be considered. However, exact thickness measurements are not possible using conventional measuring techniques.

Figure 3:
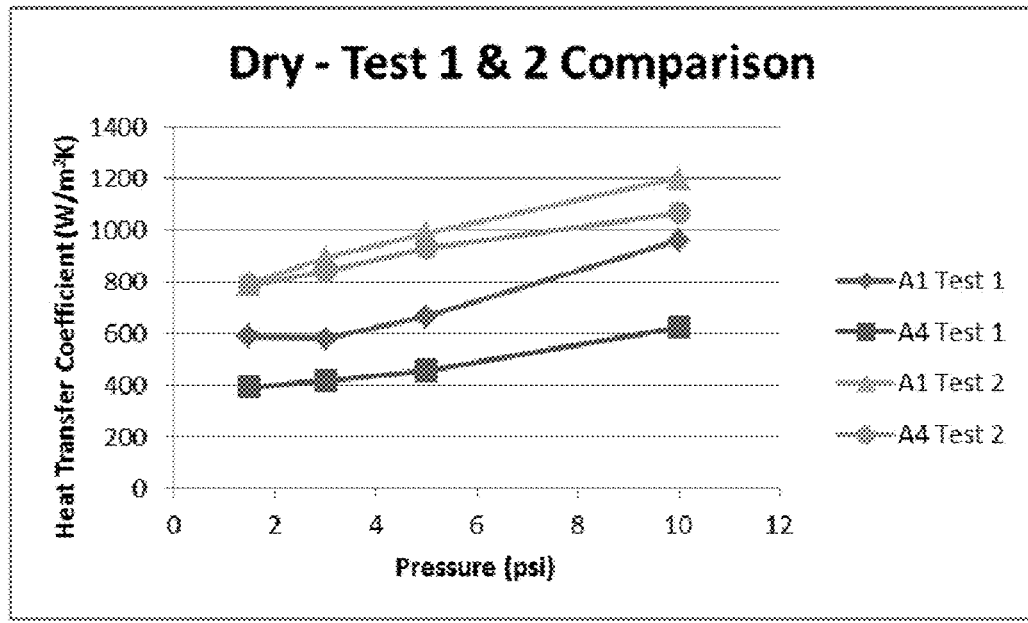
FIG. 3 is a graph showing the heat transfer coefficient for dry stacks of three TIMs on aluminum (Al) substrates over two test cycles.

Results of heat transfer testing for two dry TIM stacks are shown in FIG. 3. Each specimen was tested through the entire 10-69 kPa (1.5 to 10 psi) pressure cycle twice to assess reproducibility of the dry stacks. For both of the dry stacks tested, there was a substantial improvement in heat transfer after having experienced one pressure cycle. This suggested that an assembly pressure was required in order to ensure good contact between adjacent CNT layers. This demonstrates the improvement in heat transfer resulting from interdigitation.

Wax-Assembled Stacks:

In these experiments, three TIM specimens on aluminum substrates, each with a total thickness of approximately 200 µm, were stacked and bonded with a thin wax layer (~100 nm) to provide a TIM assembly of roughly 600 µm (0.024") in thickness. Actual displacements measured with the instrument crosshead were somewhat less than the target thickness.

Figure 4:
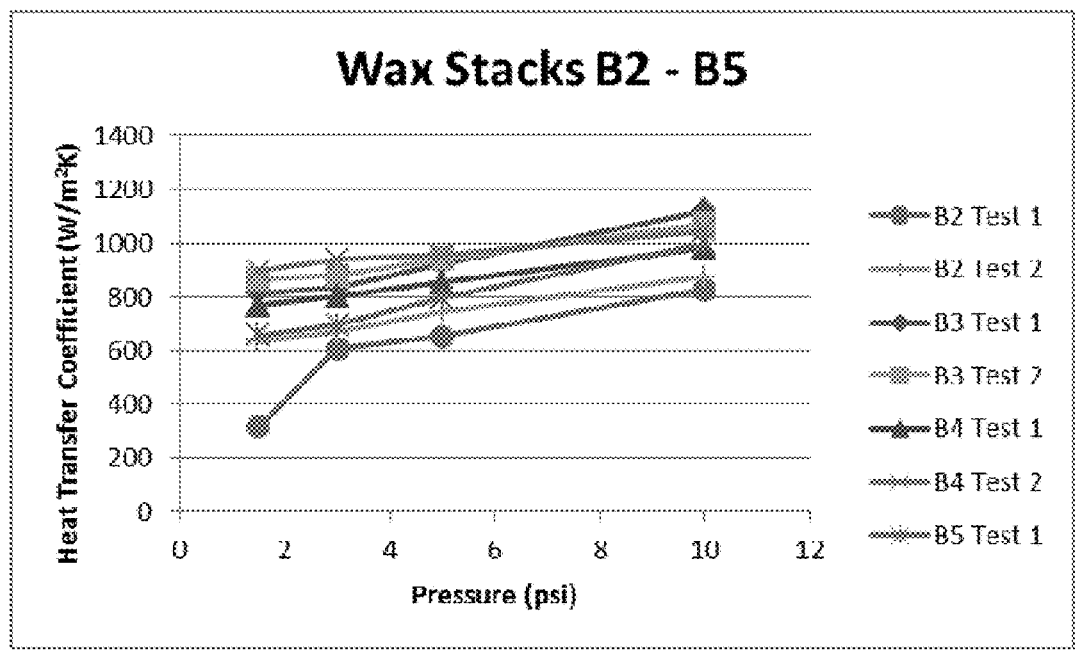
FIG. 4 is a graph showing the heat transfer coefficient for wax-bonded stacks of three TIMs on aluminum (Al) substrates over two test cycles.

Test results for the wax-bonded stacks are provided in FIG. 4. In general, the wax stacks are more consistent in performance than the dry stacks and do not appear to require a "break-in" pressure cycle before performing well. A performance anomaly was noted for specimen B2 at low contact pressure in Test 1; this might be due to insufficient contact between the upper meter block and the specimen in the fixture. Subsequent tests of this particular specimen consistently showed excellent performance.

Stacking TIMs, as described herein, allows growing long CNTs on metal substrates, especially when a thin (~nm thick) layer of polymer is used to bond the inter-tier layers and control the level of interdigitation.

Example 2: Multilayered/Multitiered CNT-Based Thermal Interface Materials (TIMs) Containing Polymer or Adhesive CNT arrays were grown to nominally 100 µm thickness and fully infiltrated with a soft polyurethane polymer. The thermal resistance of each individual pad was measured using a modified ASTM D570 stepped bar apparatus.

The individual samples were stacked using various methods, and the thermal resistance of the resulting stack was measured in the same manner as the single tiers.

First, two individual array samples with measured thermal resistances of 1.37 and 1.5 cm$^2$-K/W respectively were stacked on top of one another. Solvent known to dissolve the polymer that was used to infiltrate the array was placed between the stacks to place the interface in a liquid state. The resulting stack was allowed to dry under pressure until the solvent was fully evaporated. The stack was then measured in the stepped bar system with a resulting resistance of 1.5 cm$^2$-K/W. In this example, the thickness of the stacked array was doubled while incurring no penalty in thermal resistance.

In a second experiment, two individual array samples with thermal resistances of 0.45 and 0.66 cm$^2$-K/W respectively were stacked on top of one another. A thin layer of acrylate adhesive was placed between the samples. The sample stack was allowed to dry under pressure until the solvent was fully evaporated. The resulting stack was then measured in the stepped bar system with a resulting resistance of 0.66 cm$^2$-K/W. In this second example, the thickness of the stacked array was also doubled while incurring no penalty in thermal resistance.

Example 3: Burn-In Testing of Thermal Interface Materials (TIMs) Sample Fabrication of CNT-TIM Composite Vertically aligned carbon nanotubes were grown on 50 µm 1145 H19 aluminum foil coated on both sides with an iron catalyst via low pressure chemical vapor deposition. Acetylene and hydrogen act as precursor gases and growth is performed at 630° C. in order to stay comfortably below the melting temperature of the Al substrate. CNTs are grown to two nominal heights: 15 µm (3 min growth time) or 50 µm (15 minute growth time).

It is believed that due to the difficulty of repeatably wicking a consistent thickness of bulk paraffin wax into a CNT array, while avoiding excess polymer at the tips, a powder coating technique can more reliably deliver a uniformly thin coating of wax to the CNT tips.

The synthetic polyethylene waxes used to powder coat the CNTs were supplied in a micronized powder form that is loaded into an Eastwood Dual Voltage HotCoat powder coating gun. Dry air at 5-8 psi was delivered to the powder coating gun which provides the motive force to deliver the wax to the sample. The wax particles were electrically charged at 15 kV as they exited the gun, causing them to stick to the grounded vertically CNT forest on aluminum substrate sample prepared. The wax particles appeared to adhere well to the surface of the CNT sample, withstanding rigorous shaking and blowing. The dry coated CNT sample is then moved from the powder coating cabinet to an oven to cure (melt) the wax.

Figure 5A:
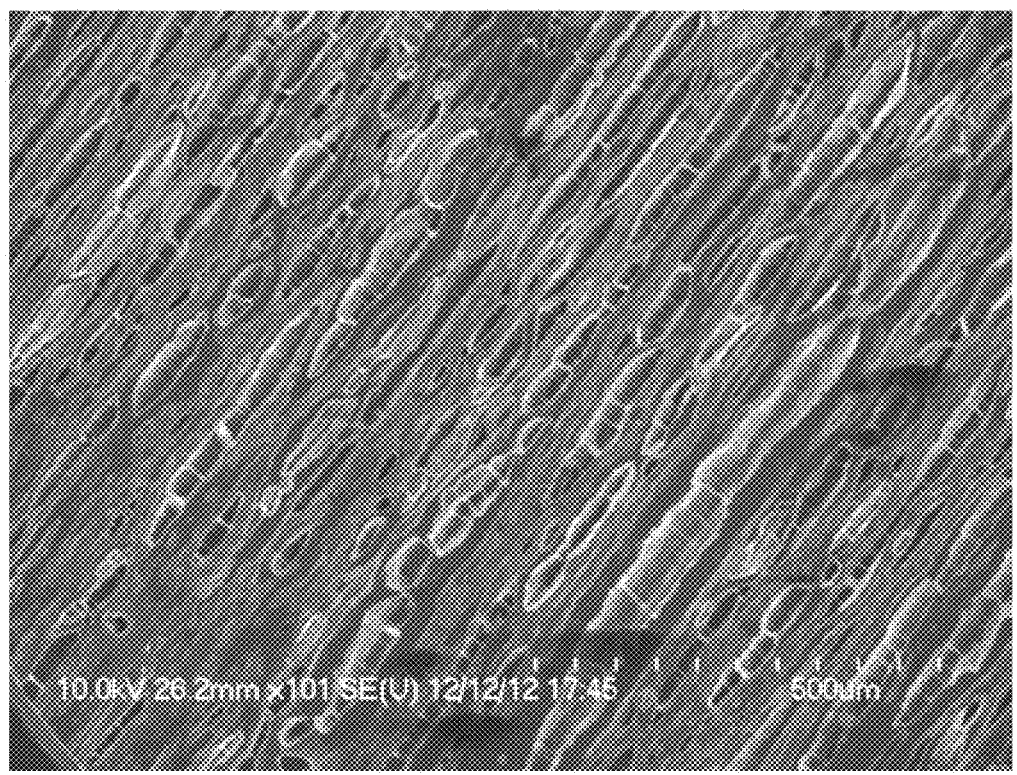
FIGS. 5A and 5B show scanning electron microscopy (SEM) images depicting capillary clumping of CNTs.
Figure 5B:
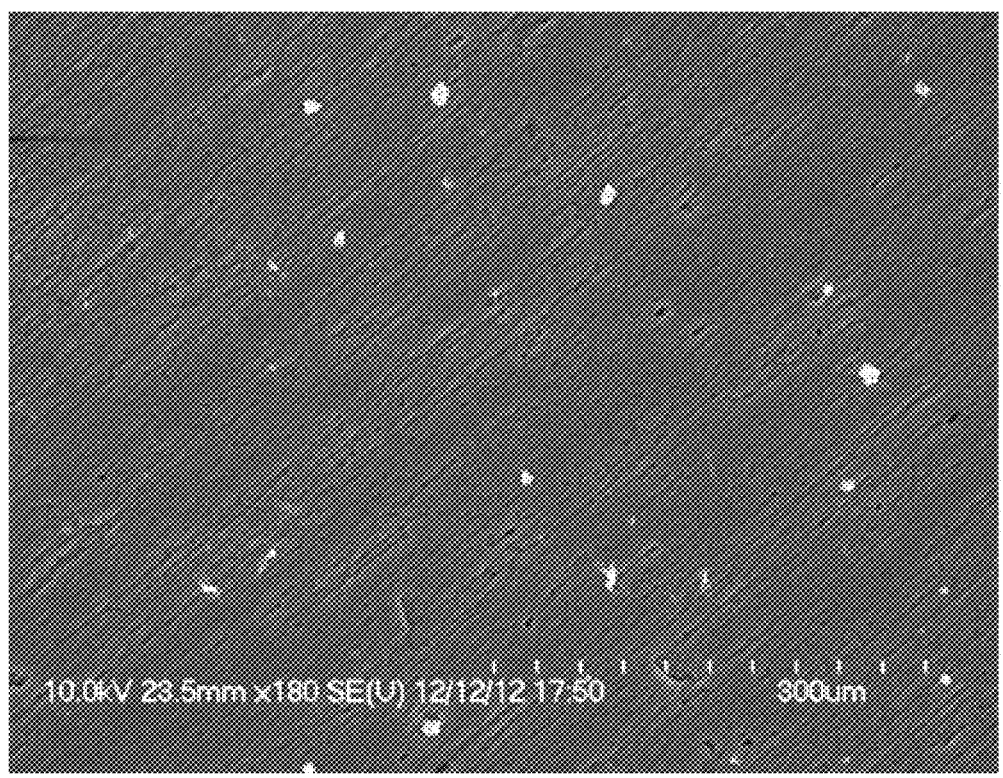

As a point of comparison, a control sample was manually coated with paraffin wax to compare coating thicknesses. Inspection of the powder coated samples using a SEM showed that there was significantly less clumping of the CNTs when using the powder coating process (FIGS. 5A and 5B). Capillary clumping of CNTs is driven by the process of drying the liquid wax that is soaked into the CNTs. The minimization of this capillary clumping suggested that the powder coating process is far more capable of delivering a thin coating of wax to enhance CNT tip contact without the excess material that leads to clumping and reduced thermal performance.

To benchmark the thermal performance of the CNT-TIM composite sample prepared against other industry standard materials, 1 cm×1 cm samples were measured in a modified ASTM-D5470 stepped bar apparatus designed to measure the steady state 1D thermal resistance of thermally conductive samples. The test apparatus is described in detail in (D. R. Thompson, S. R. Rao, and B. A. Cola, "A Stepped-Bar Apparatus for Thermal Resistance Measurements," *Journal of Electronic Packaging*, vol. 135, pp. 041002-041002, 2013). To properly establish and compare the performance of the CNT-TIM composite sample, a wide variety of commercially available TIMs were tested under the same conditions.

Figure 6A:
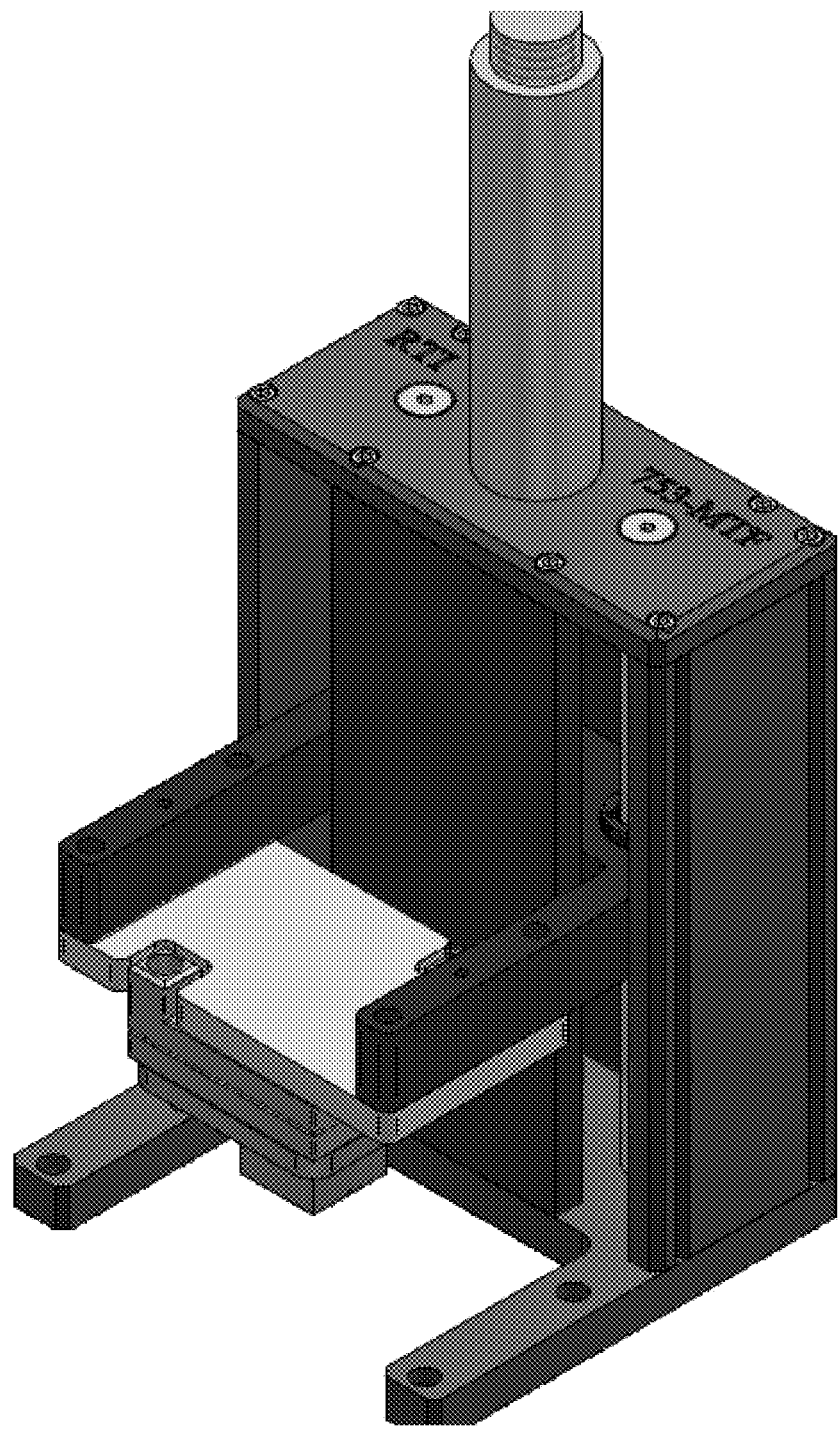
FIGS. 6A, 6B, and 6C show a detailed depiction of a non-limiting burn-in system.
Figure 6B:
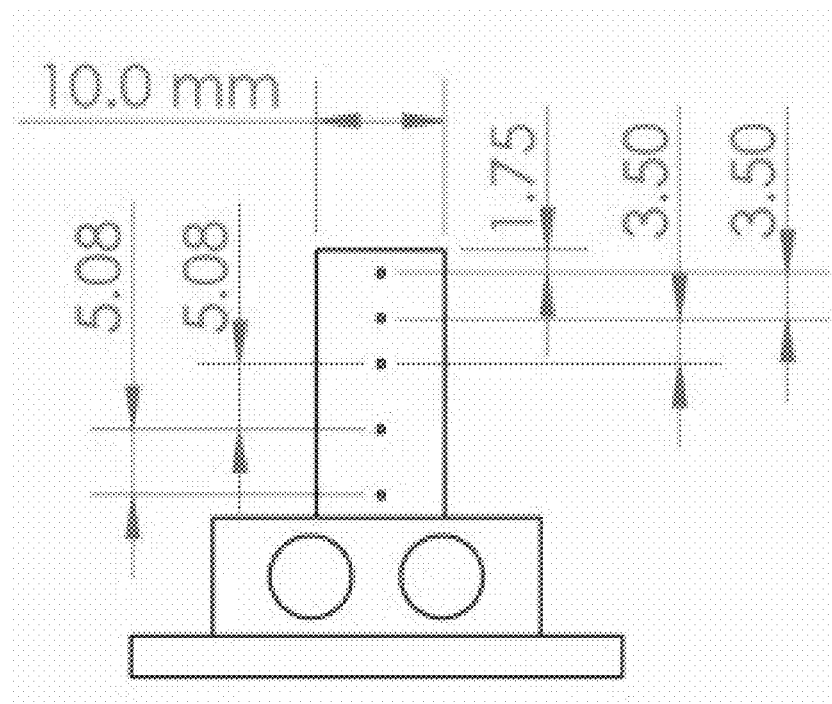
Figure 6C:
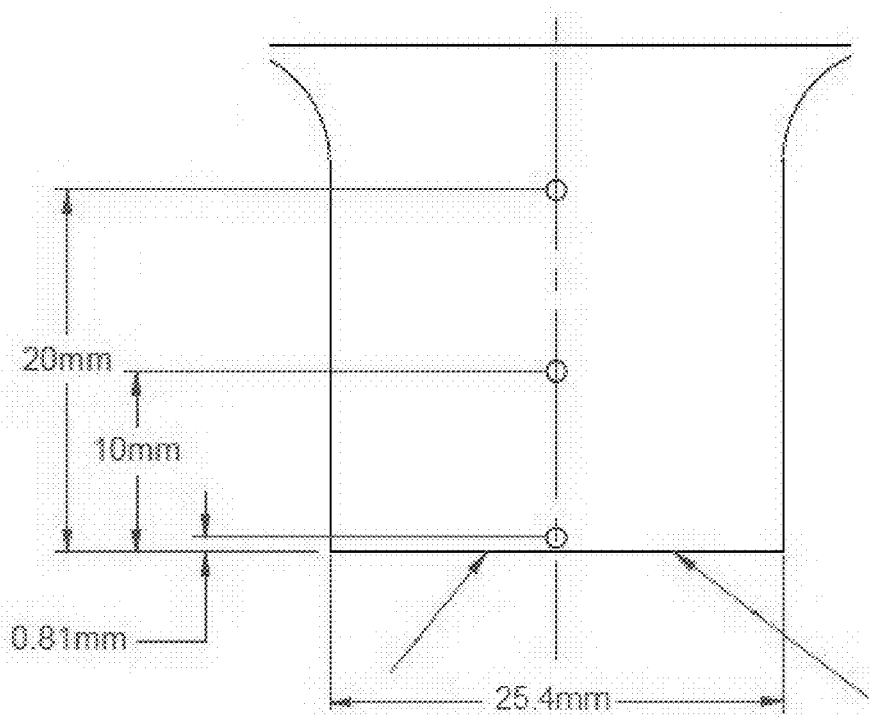

Burn-In System Design:

A burn-in system was used to simulate the thermomechanical cycles for burn-in and test applications. It was used to monitor the thermal resistance of the CNT-TIM composite sample and commercial samples over many cycles. The system is shown in FIG. 6A and the test apparatus has a lower and an upper bar, as detailed in FIGS. 6B and 6C. The lower bar is heated with two cartridge heaters and acts as the heated microchip; the upper bar is actively cooled with chilled water and acts as the cooling solution. There are five and three J-type thermocouples placed along the center of the lower and upper and upper bar, respectively. The cold plate connected to the upper bar is attached to a pneumatically driven piston. The piston is connected to a solenoid valve which is opened and closed on demand by a programmable relay that sets the cycle times. The white block is held up by a spring and rod, as shown in FIG. 6A, which is used to improve the horizontal alignment of the upper bar. Because the cold plate is attached to the actuator in a cantilevered fashion, under its own weight it tends to hang slightly below horizontal. As the cold plate strikes the white block on its downward descent, it is lifted closer to parallel giving it a more realistic strike angle with the lower meter bar. While the strike angle is lessened it does not strike the lower bar perfectly parallel, but instead has a slight pitch just as it might in a field installation. This no zero strike angle and subsequent sliding motion between the upper and lower bar causes a shear stress on the TIM as it engages and disengages, delivering a realistic wear mechanism.

With a programmable relay, the time for each cycle and between cycles can be set. In the experiments conducted, each cycle was set to 180 seconds for the bars to be engaged and 20 seconds for the bars to be disengaged. In industry, depending on the test application, a test cycle can range on the order of tens of seconds for test applications to several hours for burn in applications. An engaged time of 180 seconds was chosen because it matches the times used in the industry, and it also allots enough time for the thermal resistance to reach steady state. A 20 second disengaged time was chosen it allows for the lower bar to heat up to 120° C., which is usually the maximum operating temperature for a device under test (DUT) in industry. The set pressure for all experiments was 70 psi. The cartridge heaters are wired to a voltage regulator and it is set to the highest possible voltage so the lower bar does not exceed 120° C. The water chiller is set to 15° C.

The CNT-TIM composite sample and commercial samples to be tested were attached to the surface of the top bar with KAPTON® tape. The respective TIMs were cut to match the size of the upper bar, and four strips of tape were placed, hanging off, on the edges of the TIMs and then the tape was folded up to adhere to the upper bar.

To be able to calculate the thermal resistance, the temperatures along both bars are monitored using thermocouples wired to an Omega Data Acquisition Module. Using the position and temperature of each thermocouple, the temperature of the mating surfaces of the lower and upper bars could be calculated using a first order linear fit. The lower bar was insulated to allow for 1D conduction, and then the heat flux through the lower bar was calculated using the Equation below:

$$q'' = k_{lower\ bar}\left(\frac{dT}{dx}\right)_{lower\ bar}$$

where $k_{lower\ bar}$ is the thermal conductivity of the lower bar, and $$\left(\frac{dT}{dx}\right)$$

is the temperature gradient along the lower bar. The power input could then be calculated using the Equation below:

$$Q = q''\text{Area}_{lower\ bar}$$

The thermal resistance was determined using the Equation below:

$$R = \frac{\Delta T_{TIM}}{Q}$$

The thermal resistance was calculated after the system had reached steady state and at the same time spot in each cycle. The test was terminated once the TIM showed signs of failure (i.e., physical tearing or the resistance had greatly increased).

Figure 7:
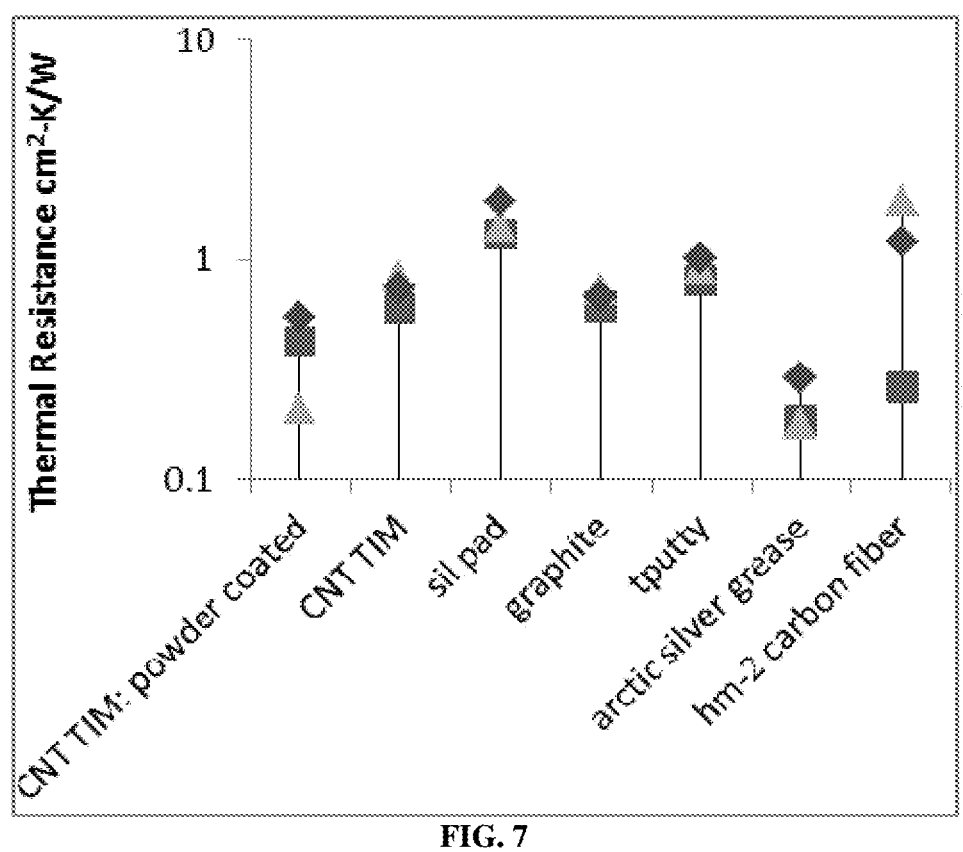
FIG. 7 is a graph showing a comparison of a CNT-TIM composite to commercially available TIM products at 50 psi.

Results:

Static Testing:

A comparison of the CNT-TIM composite sample, both with and without wax, is shown in FIG. 7 for a 50 psi contact pressure. The CNT TIM composite performance was compared to gap pads (sil pad and tputty), graphite, and high-performance thermal grease, as well as a high end carbon fiber based TIM. Across a broad spectrum of TIM types the CNT-TIM composite demonstrated the best performance in thermal resistance. At this moderate pressure the high end silver particle laden thermal grease delivered comparable performance, however the CNT-TIM composite eliminated reliability concerns associated with pump out, voiding, and delamination due to CTE mismatch. Furthermore, the CNT-TIM composite represents a drop-in coupon style solution, allowing for significant improvement in ease of application over greases or gels. Some spread in the data was evident for the powder coated CNT-TIM composite, which may be refined to ensure sample to sample uniformity and reproducibility.

Figure 8:
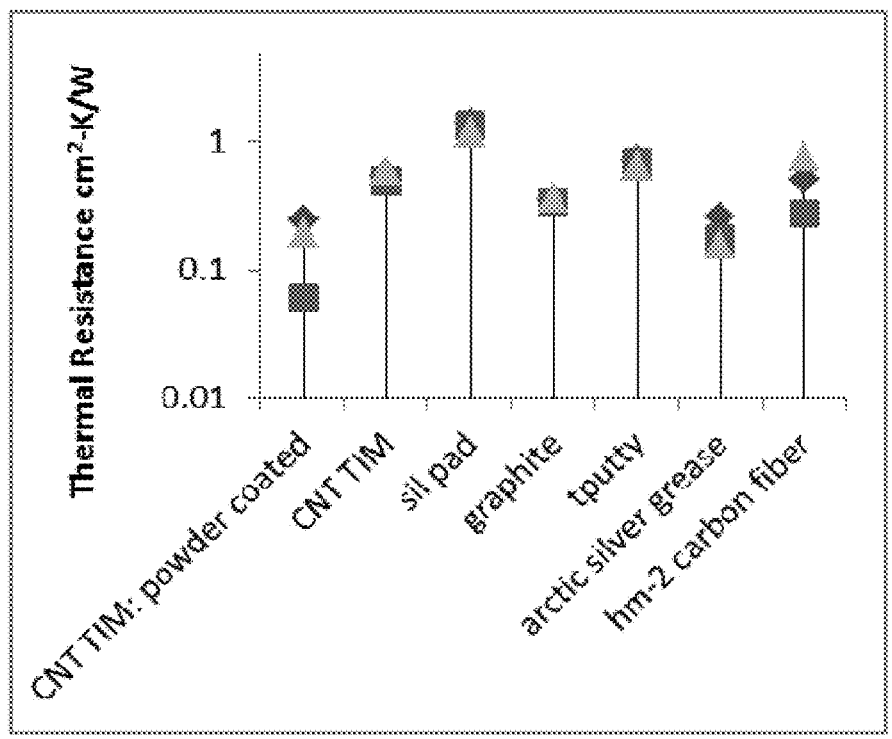
FIG. 8 is a graph showing a comparison of CNT-TIM composite to commercially available TIM products at 100 psi.

FIG. 8 shows a similar comparison, at 100 psi contact pressure. At higher contact pressures the resistances drop as expected as the bond line thickness and total contact area increase. Also, at higher contact pressure the slight advantage that the thermal grease displayed was no longer observed while the CNT-TIM composite maintains the advantages in form factor, installation and reliability that were present at lower pressures.

Burn-In and Test:

At 60 psi, the thermal resistance of the CNT-TIM composite was 0.5 cm$^2$K/W, for indium it was 0.05 cm$^2$K/W, and for rubber coated Al foil it was 0.8 cm$^2$K/W.

Figure 9:
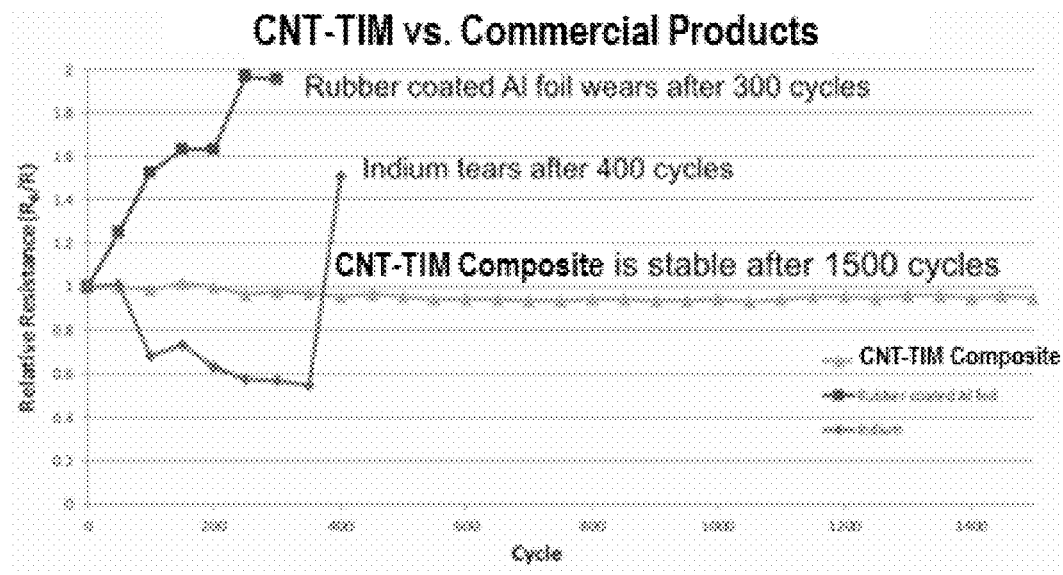
FIG. 9 is a graph showing the relative resistances of the CNT-TIM composite vs. commercially available TIM products over many cycles in the burn-in system.

FIG. 9 shows the change in resistances of the test specimens during thermo-mechanical cycling. The rubber coated aluminum foil doubled in resistance after 300 cycles because of wear, and the indium pad tore after 400 cycles. The CNT-TIM composite was still durable after 1500 cycles and the thermal resistance remained consistent. The wear from the rubber coated aluminum foil is caused from the repeated force applied to the TIM, and the rubber began to wear off exposing the underlying foil. The indium tore because of the shear force applied to the TIM described earlier. In FIG. 9, it can be noted that the indium drops in resistance before it fails; this can be attributed to the TIM 'breaking in' and creating better contact with the bars. The CNT-TIM composite had an imprint of the lower bar after 1500 cycles.

To evaluate whether the tested samples would transfer any unacceptable stains to the test die, several experiments were carried out. During the burn-in test, a glass microscope slide was placed on top of the bottom bar when the bars were disengaged. Then the top bar came down and the TIM makes contact with the glass slide. After the cycle is complete, the glass slide is inspected for residue transfer. The CNT-TIM composite did not show signs of residue transfer, while the rubber coated Al foil TIM did. The indium pad did not undergo this test because it had already stained the bottom bar during testing. To further investigate if the CNT-TIM composite would stain, another test was carried out separately from the burn-in system. The CNT-TIM composite was placed between two silicon dies under a pressure of 100 psi at 120° C. for 30 minutes. The silicon dies showed no visible signs of staining, and no signs of staining when imaged under an SEM (not shown).

Testing showed that careful selection and design polymer-carbon nanotube composites (CNT-TIM composites) could be tailored to provide a customized TIM with an optimized mixture of durability, low thermal resistance, compliance, and chemical and thermal stability.

Unless defined otherwise, all technical and scientific terms used herein have the same meanings as commonly understood by one of skill in the art to which the disclosed invention belongs. Publications cited herein and the materials for which they are cited are specifically incorporated by reference.

Those skilled in the art will recognize, or be able to ascertain using no more than routine experimentation, many equivalents to the specific embodiments of the invention described herein. Such equivalents are intended to be encompassed by the following claims.

We claim:

1. A method for making contact to a device under test with a thermally conductive and/or electrically conductive, mechanically compliant substrate having an adhesive surface, the method comprising the steps of:
    attaching the thermally conductive and/or electrically conductive, mechanically compliant substrate directly to a thermal or electrical unit head to cover an area of the thermal or electrical unit head completely or matching a size of the device under test;
    engaging the thermal or electrical unit head to the attached thermally conductive and/or electrically conductive, mechanically compliant substrate to the device under test at a pressure of at least 10 psi and at a temperature of less than 150° C.;
    holding the thermal or electrical unit head engaged to the attached thermally conductive and/or electrically conductive, mechanically compliant substrate to the device under test under the pressure of at least 10 psi for at least 1 to 300 seconds;
    disengaging and re-engaging the thermal or electrical head to the attached thermally conductive and/or electrically conductive, mechanically compliant substrate with the device under test for at least 1,500 cycles of powering up of the device under test; and
    measuring or calculating thermal resistance and/or relative thermal resistance of the device under test following cycling.

2. The method of claim 1, wherein the engaging and disengaging and re-engaging steps are repeated 10,000 to 100,000 times without removing the attached thermally conductive and/or electrically conductive, mechanically compliant substrate or having to clean debris or marks from the device under test.

3. The method of claim 1, where the device under test is tested at a temperature of between about −55° C. to 140° C.

4. The method of claim 1, wherein the adhesive surface of the thermally conductive and/or electrically conductive, mechanically compliant substrate is treated or modified to prevent mechanical sticking between the thermal or electrical unit head and the device under test.

5. The method of claim 1, wherein the thermally conductive and/or electrically conductive, mechanically compliant substrate is used to make contact to 1 to 10 dies on the same thermally conductive and/or electrically conductive, mechanically compliant substrate at a same time and wherein the 1 to 10 dies can be of different heights, shapes, and/or sizes.

6. The method of claim 1, wherein the thermally conductive and/or electrically conductive, mechanically compliant substrate adds between 0.05 and 1.5 $cm^2$ K/W of thermal resistance as measured or calculated from the measuring or calculating step.

7. The method of claim 1, wherein the thermally conductive and/or electrically conductive, mechanically compliant substrate has an in-plane thermal conductivity that is between 100 and 1,700 W/mK to spread heat from local hot spots on the device under test.

8. The method of claim 1, wherein the thermally conductive and/or electrically conductive, mechanically compliant substrate has a low thermal mass and thermal conductivity through a plane which is greater than 1, 2, 3, 4, 5, 6, 7, or 8 W/m K, and
    wherein time required to test the device under test is less than 5 min, less than 3 min, less than 1 min, or less than 30 seconds.

9. The method of claim 1, wherein the thermally conductive and/or electrically conductive, mechanically compliant substrate adds between 0.001 and 10 Ohms per $cm^2$ to the measuring or calculating step.

10. The method of claim 1, wherein the thermally conductive and/or electrically conductive, mechanically compliant substrate is applied to a pedestal or the thermal or electrical unit head prior to installation of the pedestal or the thermal or the electrical unit head to an automatic test equipment pick and place handler or to a burn-in oven.

11. The method of claim 1, wherein the thermally conductive and/or electrically conductive, mechanically compliant substrate is used to short circuit an array of electrical contact pins for characterization of the electrical contacts.

12. The method of claim 1, wherein the thermally conductive and/or electrically conductive, mechanically compliant substrate has a compression of less than 5 microns.

13. The method of claim 1, wherein the thermally conductive and/or electrically conductive, mechanically compliant substrate can be compressed to at least 5% of its original thickness with an applied pressure of less than 100 psi.

14. The method of claim 1, wherein the thermally conductive and/or electrically conductive, mechanically compliant substrate can be compressed as much as 50% of its original thickness without tearing or shear failure.

15. The method of claim 1, wherein the thermally conductive and/or electrically conductive, mechanically compliant substrate can be compressed to different amounts in different areas of the thermally conductive and/or electrically conductive, mechanically compliant substrate, while maintaining surface contact to one or more dies or chips on a board, where the one or more dies or chips on the board have different sizes, shapes, or heights.

16. The method of claim 1, wherein with an adhesive surface adhesive is a thermoplastic or pressure sensitive adhesive that is imbedded in a surface layer of the thermally conductive and/or electrically conductive, mechanically compliant substrate and does not add more than 5 microns of thickness between the thermally conductive and/or electrically conductive, mechanically compliant substrate and a contact surface while maintaining a strong mechanical bond.

17. The method of claim 1, wherein with the thermal or electrical unit head is a part of an automatic test equipment pick and place handler and the thermally conductive and/or electrically conductive, mechanically compliant substrate replaces the need for a pedestal or a device kit for different device shapes or geometries.

18. The method of claim 1, wherein the thermal or electrical unit head is a part of a burn-in oven and the thermally conductive and/or electrically conductive, mechanically compliant substrate replaces the need for a pedestal or device kit for different device shapes or geometries.

19. The method of claim 1, wherein the thermally conductive and/or electrically conductive, mechanically compliant substrate is used in combination with a metal pedestal on one or both sides of the metal pedestal.

20. The method of claim 1, wherein the thermally conductive and/or electrically conductive, mechanically compliant substrate minimizes any need to polish mating surfaces to a greater degree than a factory mill finish.

21. The method of claim 1, wherein the thermally conductive and/or electrically conductive, mechanically compliant substrate is between about 10 to 10,000 micrometers in thickness.

22. The method of claim 1, wherein the thermally conductive and/or electrically conductive, mechanically compliant substrate is less than about 100 microns in thickness.

23. The method of claim 1, wherein the thermally conductive and/or electrically conductive, mechanically compliant substrate can deform to fill a gap between the device under test and the thermal or electrical unit head when a center to edge curvature of the device under test or the thermal or electrical unit head is between about 5-200 microns.

24. The method of claim 1, wherein the thermally conductive and/or electrically conductive, mechanically compliant substrate is a vertically aligned carbon nanotube array grown on one or both sides of a metal or graphite foil or sheet.

25. The method of claim 1, wherein the thermally conductive and/or electrically conductive, mechanically compliant substrate is a multilayer stack of vertically aligned carbon nanotube array grown on one or both sides of a metal or graphite foil or sheet, wherein the number of layers is between 1 and 20.

26. The method of claim 1, wherein the thermally conductive and/or electrically conductive, mechanically compliant substrate is a flexible glass or ceramic or a dielectric foil or sheet, or a metal foil coated with a dielectric layer to provide electrical isolation.

27. The method of claim 1, wherein the thermally conductive and/or electrically conductive, mechanically compliant substrate is a vertically aligned carbon nanotube array formed using a catalyst anchored to the thermally conductive and/or electrically conductive, mechanically compliant substrate.

28. The method of claim 1, wherein the thermally conductive and/or electrically conductive, mechanically compliant substrate is precision cut to dimensions of the device under test, or to dimensions of the thermal or electrical unit head, allowing for penetration through the thermally conductive and/or electrically conductive, mechanically compliant substrate for one or more sensors, one or more mounting alignment pins, one or more vacuum chuckings, or combinations thereof.

29. The method of claim 1, wherein the thermally conductive and/or electrically conductive, mechanically compliant substrate when applied to a pedestal or the thermal or electrical unit head can be removed from the pedestal or the thermal or electrical unit head without leaving any residue or substantially any residue.

30. The method of claim 1, wherein the thermally conductive and/or electrically conductive, mechanically compliant substrate is attached permanently or semi-permanently to either a heat source or a heat sink through the use of a conformal coating of a thermoplastic adhesive, where the addition of the thermoplastic adhesive does not increase thermal resistance of the thermally conductive and/or electrically conductive, mechanically compliant substrate, as compared to the thermally conductive and/or electrically conductive, mechanically compliant substrate without adhesive.

31. The method of claim 1, wherein an adhesive surface adhesive leaves no residue or minimal residue.

32. The method of claim 1, wherein the thermally conductive and/or electrically conductive, mechanically compliant substrate is a carbon nanotube array, comprising carbon nanotubes, that is infiltrated and coated with a durable, low compression polymer where the polymer forms a coplanar coating on tips of the carbon nanotubes or has no more than 1000 nm of excess polymer above the carbon nanotube tips.

33. The method of claim 32, wherein the low compression polymer does not or substantially does not weep, sweat, evaporate, or otherwise transfer residue to the device under test.

34. The method of claim 32, wherein the low compression polymer has a high dielectric strength with high electrical resistivity.

35. The method of claim 32, wherein the carbon nanotube tips remain available to make electrical contact with a surface that it is intended to mate with.

36. The method of claim 1, wherein an adhesive surface adhesive does not add thermal or electrical resistance to the thermally conductive and/or electrically conductive, mechanically compliant substrate interface with the device under test or the thermal or electrical unit head.

37. The method of claim 1, wherein an adhesive surface adhesive is a peel and stick adhesive and/or thermally activated adhesive.

38. The method of claim 1, wherein the device is tested without removing the thermally conductive and/or electrically conductive, mechanically compliant substrate or having to clean debris or marks from the device under test.

39. The method of claim 1, wherein the thermally conductive and/or electrically conductive, mechanically compliant substrate is a coated carbon nanotube array thermal interface material (TIM).

* * * * *